(12) United States Patent
Qin et al.

(10) Patent No.: US 6,783,523 B2
(45) Date of Patent: *Aug. 31, 2004

(54) UNIFIED SYSTEMS AND METHODS FOR CONTROLLING USE AND OPERATION OF A FAMILY OF DIFFERENT TREATMENT DEVICES

(75) Inventors: Jay Qin, Fremont, CA (US); Robin Bek, Campbell, CA (US); John Gaiser, Mountain View, CA (US); Rachel Croft, San Francisco, CA (US); Peter Muller, Los Gatos, CA (US); David S Utley, Redwood City, CA (US)

(73) Assignee: Curon Medical, Inc., Fremont, CA (US)

(*) Notice: Subject to any disclaimer, the term of this patent is extended or adjusted under 35 U.S.C. 154(b) by 93 days.

This patent is subject to a terminal disclaimer.

(21) Appl. No.: 10/212,311

(22) Filed: Aug. 5, 2002

(65) Prior Publication Data

US 2002/0198519 A1 Dec. 26, 2002

Related U.S. Application Data

(63) Continuation of application No. 09/639,910, filed on Aug. 16, 2000, now abandoned, which is a continuation-in-part of application No. 09/574,704, filed on May 18, 2000, now Pat. No. 6,464,689, and a continuation-in-part of application No. 09/305,123, filed on May 4, 1999, now Pat. No. 6,358,245.

(51) Int. Cl.[7] .............................................. A61B 19/00
(52) U.S. Cl. ............................................ 606/1; 606/41
(58) Field of Search ................................ 606/1, 41, 42, 606/45–50, 32–34; 607/101, 102

(56) References Cited

U.S. PATENT DOCUMENTS

| | | |
|---|---|---|
| 1,798,902 A | 3/1931 | Raney |
| 3,517,128 A | 6/1970 | Hines |
| 3,901,241 A | 8/1975 | Allen, Jr. |
| 4,011,872 A | 3/1977 | Komiya |
| 4,196,724 A | 4/1980 | Wirt et al. |
| 4,411,266 A | 10/1983 | Cosman |
| 4,423,812 A | 1/1984 | Sato |
| 4,532,924 A | 8/1985 | Auth et al. |
| 4,565,200 A | 1/1986 | Cosman |

(List continued on next page.)

FOREIGN PATENT DOCUMENTS

| | | |
|---|---|---|
| DE | 43 03 882 | 2/1995 |
| DE | 38 38 840 | 2/1997 |
| EP | 0 139 607 | 5/1985 |

(List continued on next page.)

OTHER PUBLICATIONS

Castell, D.O. Gastroesophageal Reflux Disease: Current Stragegies for Patient Management : Arch Fam. Med 5(4): 221–7.

Dallemagne, B. et al., "Laparoscopic Nissen Fundoplication: Preliminary, " Surgical Laparoscopy & Endoscopy. 1991 1(3): 138–43.

Kelly, KA et al., "Duodenal–gastric reflux and slowed gastric emptying by electrical pacing of the canine duodenal pacesetter potential," Gastroenterology. 1997.72(3): 429–33.

(List continued on next page.)

*Primary Examiner*—Michael Peffley
(74) *Attorney, Agent, or Firm*—Ryan Kromholz & Manion, S.C.

(57) ABSTRACT

Unified systems and methods enable control of the use and operation of a family of different treatment devices, to treat dysfunction in different regions of the body.

25 Claims, 27 Drawing Sheets

U.S. PATENT DOCUMENTS

| | | |
|---|---|---|
| 4,705,041 A | 11/1987 | Kim |
| 4,858,615 A | 8/1989 | Meinema |
| 4,901,737 A | 2/1990 | Toone |
| 4,906,203 A | 3/1990 | Margrave et al. |
| 4,907,589 A | 3/1990 | Cosman |
| 4,943,290 A | 7/1990 | Rexroth et al. |
| 4,947,842 A | 8/1990 | Marchosky et al. |
| 4,955,377 A | 9/1990 | Lennox et al. |
| 4,966,597 A | 10/1990 | Cosman |
| 4,976,711 A | 12/1990 | Parins et al. |
| 5,019,075 A | 5/1991 | Spears et al. |
| 5,035,696 A | 7/1991 | Rydell |
| 5,046,512 A | 9/1991 | Murchie |
| 5,047,028 A | 9/1991 | Qian |
| 5,057,107 A | 10/1991 | Parins et al. |
| 5,078,717 A | 1/1992 | Parins et al. |
| 5,083,565 A | 1/1992 | Parins |
| 5,084,044 A | 1/1992 | Quint |
| 5,088,979 A | 2/1992 | Filipi et al. |
| 5,094,233 A | 3/1992 | Brennan |
| 5,100,423 A | 3/1992 | Fearnot |
| 5,106,360 A | 4/1992 | Ishiwara et al. |
| 5,122,137 A | 6/1992 | Lennox |
| 5,125,928 A | 6/1992 | Parins et al. |
| 5,156,151 A | 10/1992 | Imran |
| 5,190,541 A | 3/1993 | Abele et al. |
| 5,197,963 A | 3/1993 | Parins |
| 5,197,964 A | 3/1993 | Parins |
| 5,205,287 A | 4/1993 | Erbel et al. |
| 5,215,103 A | 6/1993 | Desai |
| 5,232,444 A | 8/1993 | Just et al. |
| 5,233,515 A | 8/1993 | Cosman |
| 5,236,413 A | 8/1993 | Fiering |
| 5,242,441 A | 9/1993 | Avitall |
| 5,254,126 A | 10/1993 | Filipi et al. |
| 5,256,138 A | 10/1993 | Vurek et al. |
| 5,257,451 A | 11/1993 | Edwards et al. |
| 5,263,493 A | 11/1993 | Avitall |
| 5,275,162 A | 1/1994 | Edwards et al. |
| 5,275,608 A | 1/1994 | Forman et al. |
| 5,275,610 A | 1/1994 | Eberbach |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,292,321 A | 3/1994 | Lee |
| 5,293,869 A | 3/1994 | Edwards et al. |
| 5,309,910 A | 5/1994 | Edwards et al. |
| 5,313,943 A | 5/1994 | Houser et al. |
| 5,314,466 A | 5/1994 | Stern et al. |
| 5,316,020 A | 5/1994 | Truffer |
| 5,324,284 A | 6/1994 | Imran |
| 5,328,467 A | 7/1994 | Edwards et al. |
| 5,334,196 A | 8/1994 | Scott et al. |
| 5,336,222 A | 8/1994 | Durgin, Jr. et al. |
| 5,345,936 A | 9/1994 | Pomeranz et al. |
| 5,348,554 A | 9/1994 | Imran et al. |
| 5,363,861 A | 11/1994 | Edwards et al. |
| 5,365,926 A | 11/1994 | Desai |
| 5,365,945 A | 11/1994 | Halstrom |
| 5,366,490 A | 11/1994 | Edwards et al. |
| 5,368,557 A | 11/1994 | Nita et al. |
| 5,368,592 A | 11/1994 | Stern et al. |
| 5,370,675 A | 12/1994 | Edwards et al. |
| 5,370,678 A | 12/1994 | Edwards et al. |
| 5,383,874 A | 1/1995 | Jackson et al. |
| 5,383,876 A | 1/1995 | Nardella |
| 5,383,917 A | 1/1995 | Desai et al. |
| 5,385,544 A | 1/1995 | Edwards et al. |
| 5,397,339 A | 3/1995 | Desai |
| 5,398,683 A | 3/1995 | Edwards et al. |
| 5,401,272 A | 3/1995 | Perkins |
| 5,403,311 A | 4/1995 | Abele et al. |
| 5,409,453 A | 4/1995 | Lundquist et al. |
| 5,409,483 A | 4/1995 | Campbell et al. |
| 5,415,657 A | 5/1995 | Taymor-Luria |
| 5,421,819 A | 6/1995 | Edwards et al. |
| 5,423,808 A | 6/1995 | Edwards et al. |
| 5,423,812 A | 6/1995 | Ellman et al. |
| 5,433,739 A | 7/1995 | Sluijter et al. |
| 5,435,805 A | 7/1995 | Edwards |
| 5,441,499 A | 8/1995 | Fritzsch |
| 5,443,470 A | 8/1995 | Stern et al. |
| 5,456,662 A | 10/1995 | Edwards et al. |
| 5,456,682 A | 10/1995 | Edwards et al. |
| 5,458,596 A | 10/1995 | Lax et al. |
| 5,458,597 A | 10/1995 | Edwards et al. |
| 5,465,717 A | 11/1995 | Imran et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,520,684 A | 5/1996 | Imran |
| 5,531,676 A | 7/1996 | Edwards et al. |
| 5,531,677 A | 7/1996 | Lundquist et al. |
| 5,536,240 A | 7/1996 | Edwards et al. |
| 5,536,267 A | 7/1996 | Edwards et al. |
| 5,540,655 A | 7/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,599,345 A | 2/1997 | Edwards et al. |
| 5,609,151 A | 3/1997 | Mulier et al. |
| 5,624,439 A | 4/1997 | Edwards et al. |
| 5,651,780 A | 7/1997 | Jackson et al. |
| 5,672,153 A | 9/1997 | Lax et al. |
| 5,676,674 A | 10/1997 | Bolanos et al. |
| 5,688,266 A | 11/1997 | Edwards et al. |
| 5,688,490 A | 11/1997 | Tournier et al. |
| 5,702,438 A | 12/1997 | Avitall |
| 5,709,224 A | 1/1998 | Behl et al. |
| 5,732,698 A | 3/1998 | Swanson et al. |
| 5,738,096 A | 4/1998 | Ben-Haim |
| 5,742,718 A | 4/1998 | Harman et al. |
| 5,743,903 A | 4/1998 | Stern et al. |
| 5,830,213 A | 11/1998 | Panescu et al. |
| 5,836,874 A | 11/1998 | Swanson et al. |
| 5,848,969 A | 12/1998 | Panescu et al. |
| 5,860,974 A | 1/1999 | Abele |
| 5,871,483 A | 2/1999 | Jackson et al. |
| 5,891,030 A | 4/1999 | Johnson et al. |
| 5,916,163 A | 6/1999 | Panescu et al. |

| | | |
|---|---|---|
| 5,931,835 A | 8/1999 | Mackey |
| 5,957,961 A | 9/1999 | Maguire et al. |
| 6,004,269 A | 12/1999 | Crowley et al. |
| 6,014,581 A | 1/2000 | Whayne et al. |
| 6,023,638 A | 2/2000 | Swanson |
| 6,106,460 A | 8/2000 | Panescu et al. |
| 6,165,169 A | 12/2000 | Panescu et al. |
| 6,358,245 B1 | 3/2002 | Edwards et al. |
| 6,464,689 B1 * | 10/2002 | Qin et al. .................. 606/1 |

FOREIGN PATENT DOCUMENTS

| | | |
|---|---|---|
| EP | 0 608 609 | 8/1994 |
| WO | 91/01773 | 2/1991 |
| WO | 92/10142 | 6/1992 |
| WO | 93/08755 | 5/1993 |
| WO | 94/10925 | 5/1994 |
| WO | 94/21165 | 9/1994 |
| WO | 94/21178 | 9/1994 |
| WO | 94/22366 | 10/1994 |
| WO | 94/26178 | 11/1994 |
| WO | 95/18575 | 7/1995 |
| WO | 95/19142 | 7/1995 |
| WO | 95/25472 | 9/1995 |
| WO | 96/00042 | 1/1996 |
| WO | 96/16606 | 1/1996 |
| WO | 96/29946 | 1/1996 |
| WO | 97/06857 | 2/1997 |
| WO | 97/32532 | 9/1997 |
| WO | 97/43971 | 11/1997 |

OTHER PUBLICATIONS

Reynolds, J.C. "Influence of pathophysiology, severity, and cost on the medical management of gastroesophageal reflux disease," Am J. Health–Syst Pharm. 53(22 suppl 3): S5–12.

Urschel, J.D. "Complications of Antireflux Surgery," Am J. Surg. 1993. 166(1): 68–70.

Kaneko, et al., Physiological Laryngeal Pacemaker, May 1985, Trans Am Soc. Artif. Intern Organs, vol. XXXI, pp. 293–296.

Mugica et al. Direct Diaphragm Stimulation, Jan. 1987 PACE, vol. 10, pp. 252–256.

Mugica et al., Neurostimulation: An Overview, Chapter 21, Preliminary Test of a Muscular Diaphragm Pacing System on Human Patients. 1985. pp. 3. 263–279.

Rice et al., Endoscopic Paranasal Sinus Surgery, Chapter 5, Endoscopic Paranasal Sinus Surgery, The Technique of Messerklinger, Raven Press, 1988, pp. 75–104.

Rice et al., Endoscopic Paranasal Sinus Surgery, Chapter 6, Functional Endoscopic Paranasal Sinus Surgery, The Technique of Wigand, Raven Press, 1988, pp. 105–125.

Karlstrom, L.H. et al, Exotopic jejunal pacemakers and enterogastric reflux after Roux gastrectomy; Effect of intestinal pacing. Surgery 1989. 106(3): 486–495.

Hinder; R.A. et al. "The Technique of Laparoscopic Nissen Fundoplication," Surgical Laparoscopy & Endoscopy. 1992.2(3): 265–272.

* cited by examiner

US 6,783,523 B2

UNIFIED SYSTEMS AND METHODS FOR CONTROLLING USE AND OPERATION OF A FAMILY OF DIFFERENT TREATMENT DEVICES

RELATED APPLICATIONS

This application is a continuation of U.S. patent application Ser. No. 09/639,910, filed Aug. 16, 2000, (now abandoned) which is a continuation-in-part of U.S. patent application Ser. No. 09/305,123, filed May 4, 1999, now U.S. Pat. No. 6,358,245, and which is also a continuation-in-part of U.S. patent application Ser. No. 09/574,704, filed May 18, 2000 now U.S. Pat. No. 6,464,689.

FIELD OF THE INVENTION

In a general sense, the invention is directed to systems and methods for treating interior tissue regions of the body. More specifically, the invention is directed to systems and methods for treating dysfunction in body sphincters and adjoining tissue.

BACKGROUND OF THE INVENTION

The gastrointestinal (GI) tract, also called the alimentary canal, is a long tube through which food is taken into the body and digested. The alimentary canal begins at the mouth, and includes the pharynx, esophagus, stomach, small and large intestines, and rectum. In human beings, this passage is about 30 feet (9 meters) long.

Small, ring-like muscles, called sphincters, surround portions of the alimentary canal. In a healthy person, these muscles contract or tighten in a coordinated fashion during eating and the ensuing digestive process, to temporarily close off one region of the alimentary canal from another region of the alimentary canal.

For example, a muscular ring called the lower esophageal sphincter (or LES) surrounds the opening between the esophagus and the stomach. Normally, the lower esophageal sphincter maintains a high-pressure zone between fifteen and thirty mm Hg above intragastric pressures inside the stomach.

In the rectum, two muscular rings, called the internal and external sphincter muscles, normally keep fecal material from leaving the anal canal. The external sphincter muscle is a voluntary muscle, and the internal sphincter muscle is an involuntary muscle. Together, by voluntary and involuntary action, these muscles normally contract to keep fecal material in the anal canal.

Dysfunction of a sphincter in the body can lead to internal damage or disease, discomfort, or otherwise adversely affect the quality of life. For example, if the lower esophageal sphincter fails to function properly, stomach acid may rise back into the esophagus. Heartburn or other disease symptoms, including damage to the esophagus, can occur. Gastrointestinal reflux disease (GERD) is a common disorder, characterized by spontaneous relaxation of the lower esophageal sphincter.

Damage to the external or internal sphincter muscles in the rectum can cause these sphincters to dysfunction or otherwise lose their tone, such that they can no longer sustain the essential fecal holding action. Fecal incontinence results, as fecal material can descend through the anal canal without warning, stimulating the sudden urge to defecate. The physical effects of fecal incontinence (i.e., the loss of normal control of the bowels and gas, liquid, and solid stool leakage from the rectum at unexpected times) can also cause embarrassment, shame, and a loss of confidence, and can further lead to mental depression.

SUMMARY OF THE INVENTION

The invention provides unified systems and methods for controlling use and operation of a family of different treatment devices.

One aspect of the invention provides systems and method for controlling operation of a family of treatment devices comprising at least first and second different treatment devices. In use, the different treatment devices are intended to be individually deployed in association with different tissue regions. According to this aspect of the invention, the systems and methods make use of a single, unified controller to which a selected one of the first or second treatment device is coupled for use. A reader downloads information to the controller to identify the selected treatment device that is coupled to the connector. The controller enables a first control function when the reader identifies the first treatment device as the selected treatment device. The controller enables a second control function when the reader identifies the second treatment device as the selected treatment device. The single, unified controller further includes an operating system to execute on a display screen different graphical interfaces, each tailored to the configuration and treatment objectives of the particular treatment device selected for use. A first graphical interface tailored for the first treatment device is executed when the first control function is enabled. A second graphical interface tailored for the second treatment device and different, at least in part, from the first graphical interface, is executed when the second control function is enabled.

The single, unified controller thereby makes possible the treatment of different regions of the body by different treatment devices.

Another aspect of the invention provides systems and methods for controlling operation of a treatment device. The systems and methods confirm by different mechanisms the identity of the treatment device intended to be used, before enabling such use. In one embodiment, the systems and methods provide a usage key card for the treatment device. The usage key card is adapted to be handled separate from the treatment device. The usage key card contains a storage medium formatted to contain an identification code that identifies the treatment device. The identification code is communicated by a reader to a controller to which the treatment device is coupled for use. The systems and methods also provide an electrical identification signal that is communicated by the treatment device itself to the controller when the treatment device is coupled to the controller for use. Before enabling use of the treatment device, the systems and methods cross-check the identity of the treatment device based upon the identification code and based upon the electrical identification signal. The systems and methods enable use of the treatment device only when the identity of the treatment device based upon identification code and the electrical identification signal corresponds. The systems and methods thereby provide a failsafe means for identifying the treatment device, using both software (i.e., the identification code on the usage key card) and hardware (i.e., the electrical identification signal provided by the device itself).

Features and advantages of the inventions are set forth in the following Description and Drawings, as well as in the appended claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This Specification discloses various systems and methods for treating dysfunction of sphincters and adjoining tissue regions in the body. The systems and methods are particularly well suited for treating these dysfunctions in the upper and lower gastrointestinal tract, e.g., gastro-esophageal reflux disease (GERD) affecting the lower esophageal sphincter and adjacent cardia of the stomach, or fecal incontinence affecting the internal and external sphincters of the anal canal. For this reason, the systems and methods will be described in this context.

Still, it should be appreciated that the disclosed systems and methods are applicable for use in treating other dysfunctions elsewhere in the body, and dysfunctions that are not necessarily sphincter-related. For example, the various aspects of the invention have application in procedures requiring treatment of hemorrhoids, or urinary incontinence, or restoring compliance to or otherwise tightening interior tissue or muscle regions. The systems and methods that embody features of the invention are also adaptable for use with systems and surgical techniques that catheter-based and not necessarily catheter-based.

I. Overview of the System

Figure 1:
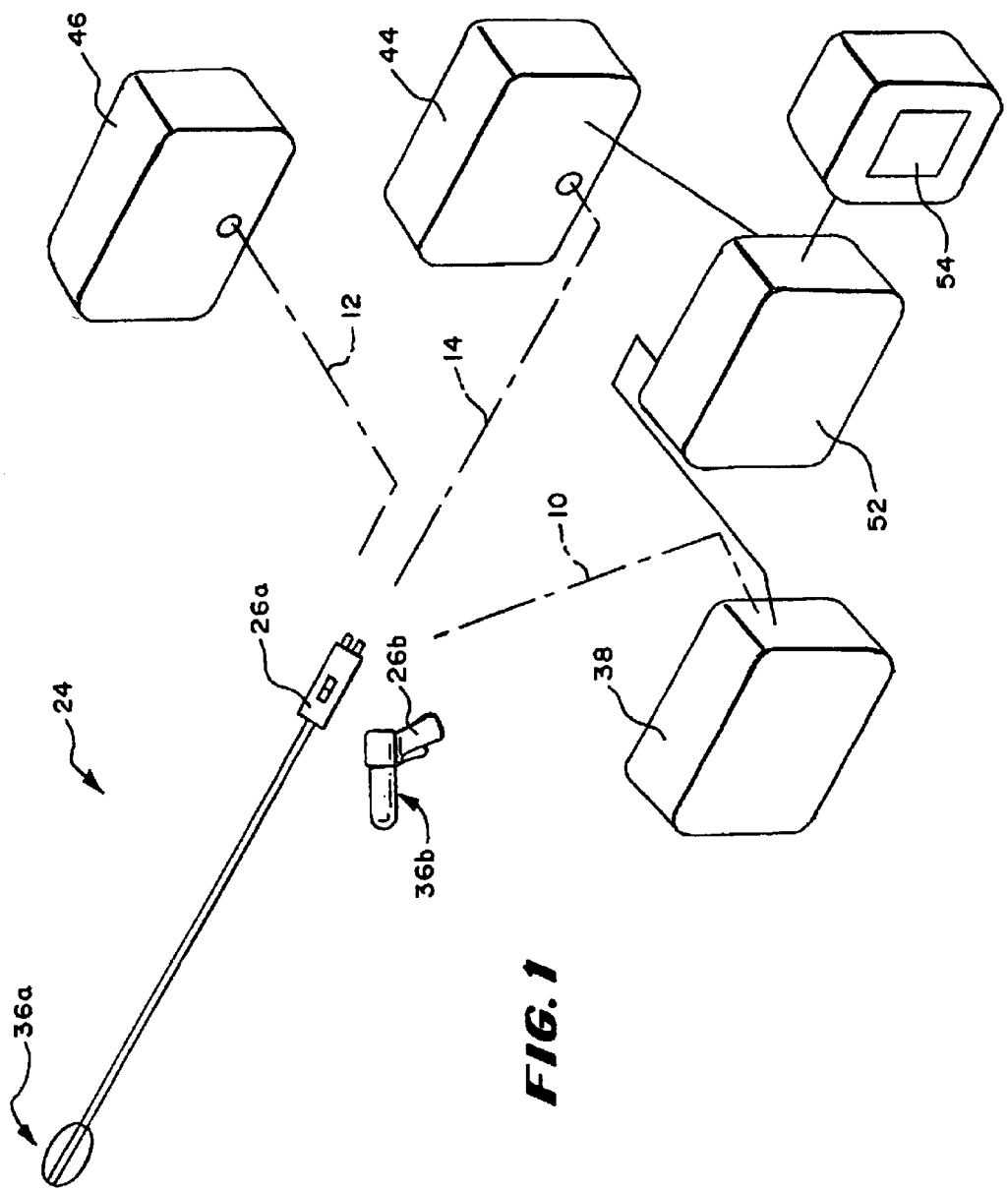
FIG. 1 is a diagrammatic view of a unified system usable in association with a family of different treatment devices for treating body sphincters and adjoining tissue regions in different regions of the body, which embodies features of the invention.

FIG. 1 shows a unified system 24 for diagnosing and/or treating dysfunction of sphincters and adjoining tissue in different regions of the body. In the illustrated embodiment, the system 24 is configured to diagnose and treat dysfunction in at least two distinct sphincter regions within the body.

The targeted sphincter regions can vary. In the illustrated embodiment, one region comprises the upper gastro-intestinal tract, e.g., the lower esophageal sphincter and adjacent cardia of the stomach. The second region comprises the lower gastrointestinal tract, e.g., in the intestines, rectum and anal canal.

The system 24 includes a family of treatment devices 26a and 26b. Each device 26a and 26b can be specifically configured according to the physiology and anatomy of the particular sphincter region which it is intended to treat. The details of construction of each device 26a and 26b will be generally described later for purposes of illustration, but are not material to the invention.

Each device 26a/26b carries an operative element 36a and 36b. The operative element 36a and 36b can be differently configured according to the physiology and anatomy of the particular sphincter region which it is intended to treated. Still, if the anatomy and physiology of the two treatment regions are the same or similar enough, the configuration of the operative elements 36a and 36b can be same or essentially the same.

In the illustrated embodiment, the operative elements 36a and 36b function in the system 10 to apply energy in a selective fashion to tissue in or adjoining the targeted sphincter region. The applied energy creates one or more lesions, or a prescribed pattern of lesions, below the surface of the targeted region. The subsurface lesions are desirably formed in a manner that preserves and protects the surface against thermal damage.

Natural healing of the subsurface lesions leads to a physical tightening of the targeted tissue. The subsurface lesions can also result in the interruption of aberrant electrical pathways that may cause spontaneous sphincter relaxation. In any event, the treatment can restore normal closure function to the sphincter region 18.

The system 24 includes a generator 38 to supply the treatment energy to the operative element 36a/36b of the device 26a/26b selected for use. In the illustrated embodiment, the generator 38 supplies radio frequency energy, e.g., having a frequency in the range of about 400 kHz to about 10 mHz. Of course, other forms of energy can be applied, e.g., coherent or incoherent light; heated or cooled fluid; resistive heating; microwave; ultrasound; a tissue ablation fluid; or cryogenic fluid.

A selected device 26a/26b can be individually coupled to the generator 38 via a cable 10 to convey the generated energy to the respective operative element 36a/36b.

The system 24 preferably also includes certain auxiliary processing equipment. In the illustrated embodiment, the processing equipment comprises an external fluid delivery apparatus 44 and an external aspirating apparatus 46.

A selected device 26a/26b can be connected via tubing 12 to the fluid delivery apparatus 44, to convey processing fluid for discharge by or near the operative element 36a/36b. A selected device 26a/26b can also be connected via tubing 14 to the aspirating apparatus 46, to convey aspirated material from or near from the operative element 36a/36b for discharge.

The system 24 also includes a controller 52. The controller 52, which preferably includes a central processing unit (CPU), is linked to the generator 38, the fluid delivery apparatus 44, and the aspirating apparatus 46. Alternatively, the aspirating apparatus 46 can comprise a conventional vacuum source typically present in a physician's suite, which operates continuously, independent of the controller 52.

The controller 52 governs the power levels, cycles, and duration that the radio frequency energy is distributed to the particular operative element 36a/36b, to achieve and maintain power levels appropriate to achieve the desired treatment objectives. In tandem, the controller 52 also desirably governs the delivery of processing fluid and, if desired, the removal of aspirated material.

The controller 52 includes an input/output (I/O) device 54. The I/O device 54 allows the physician to input control and processing variables, to enable the controller to generate appropriate command signals. The I/O device 54 also receives real time processing feedback information from one or more sensors associated with the operative element (as will be described later), for processing by the controller 52, e.g., to govern the application of energy and the delivery of processing fluid.

The I/O device 54 also includes a graphical user interface (GUI), to graphically present processing information to the physician for viewing or analysis. Further details regarding the GUI will be provided later.

II. The Treatment Devices

The structure of the operative element 36 can vary. Various representative embodiments will be described.

A. For Treatment of Upper Gastro-Intestinal Tract

Figure 2:
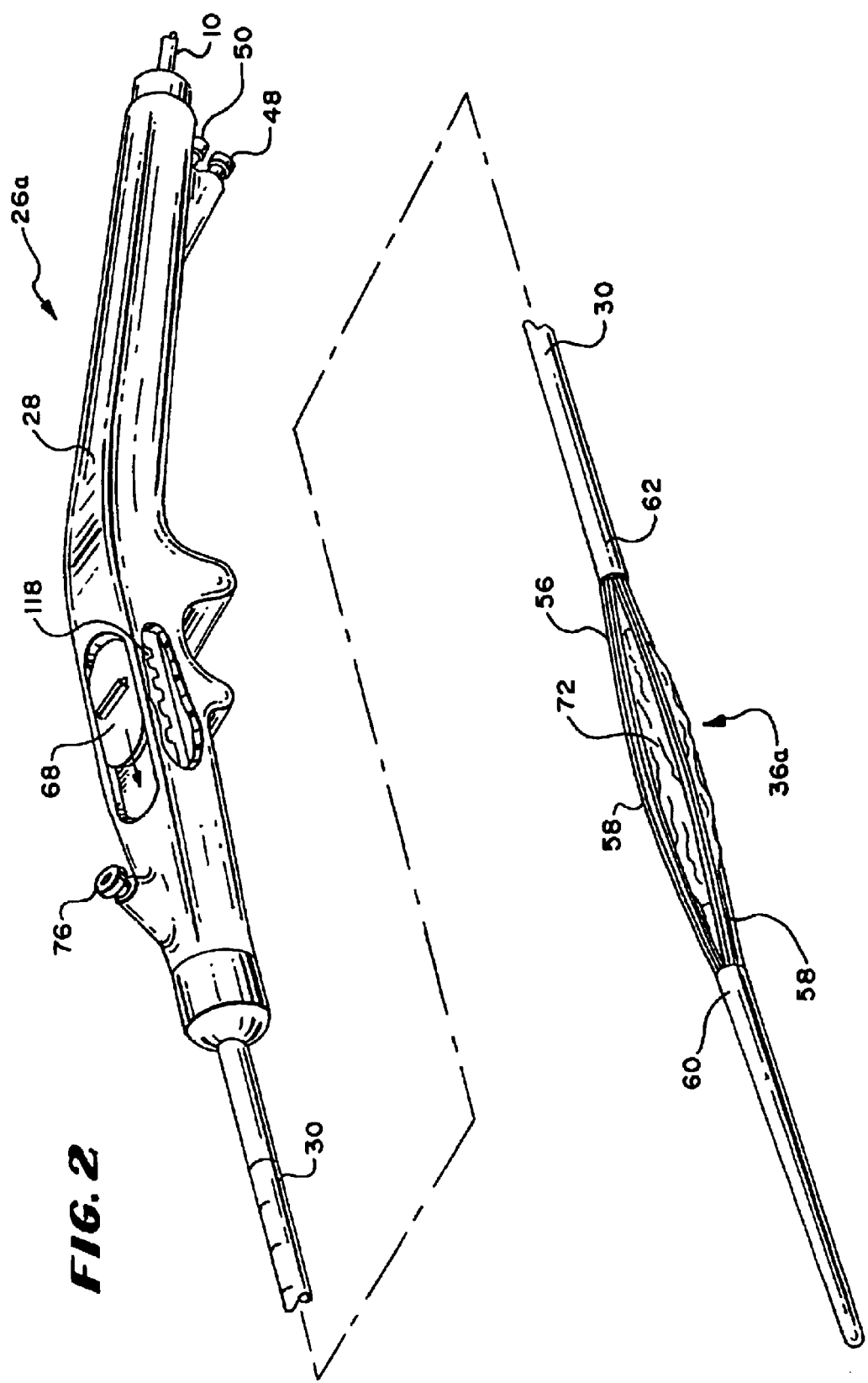
FIG. 2 is a perspective view, with portions broken away, of one type of treatment device usable in association with the system shown in FIG. 1 to treat tissue in the upper gastro-intestinal tract, the treatment device having an operative element for contacting tissue shown in a collapsed condition.
Figure 3:
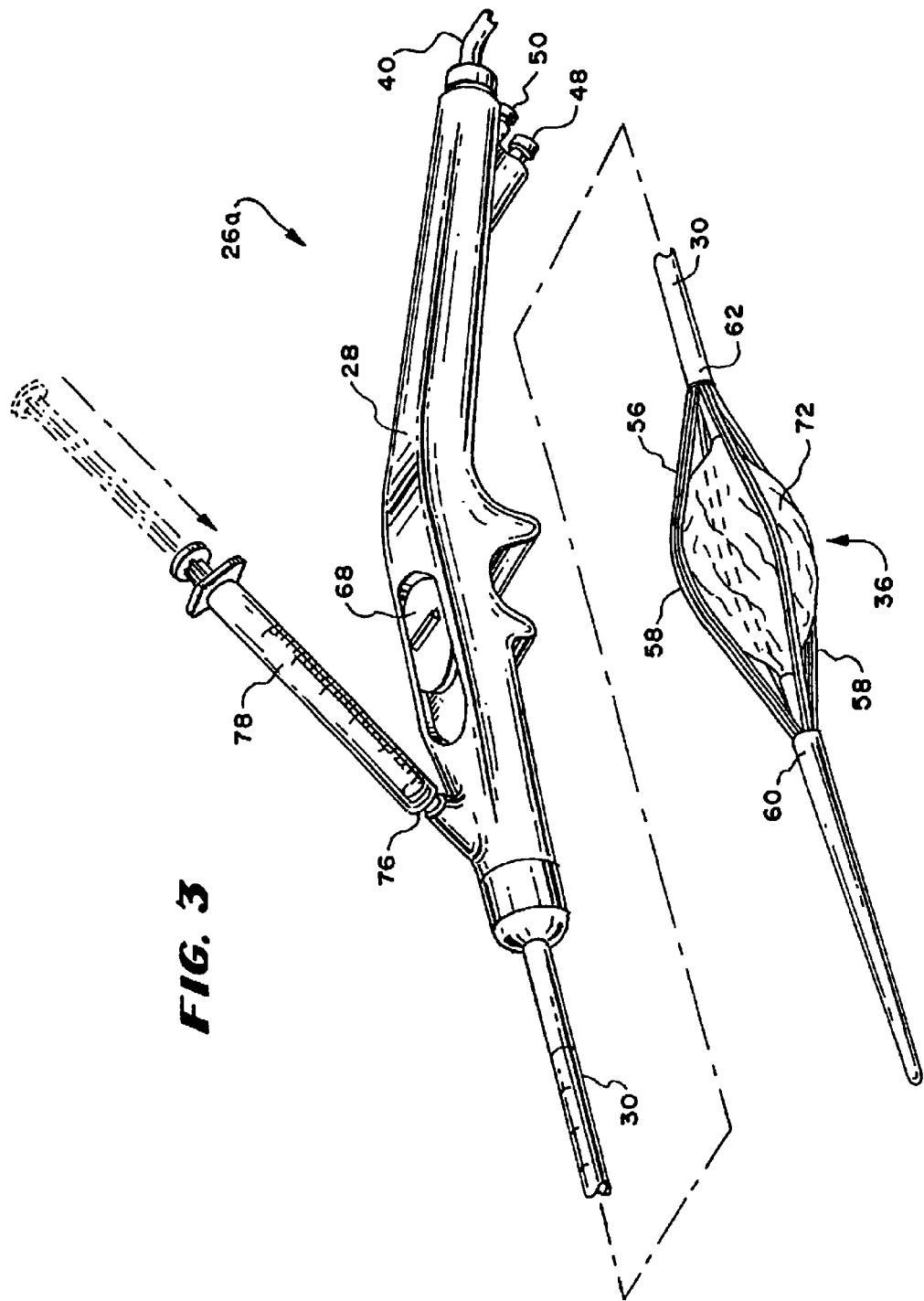
FIG. 3 is a perspective view, with portions broken away, of the device shown in FIG. 2, with the operative element shown in an expanded condition.
Figure 4:
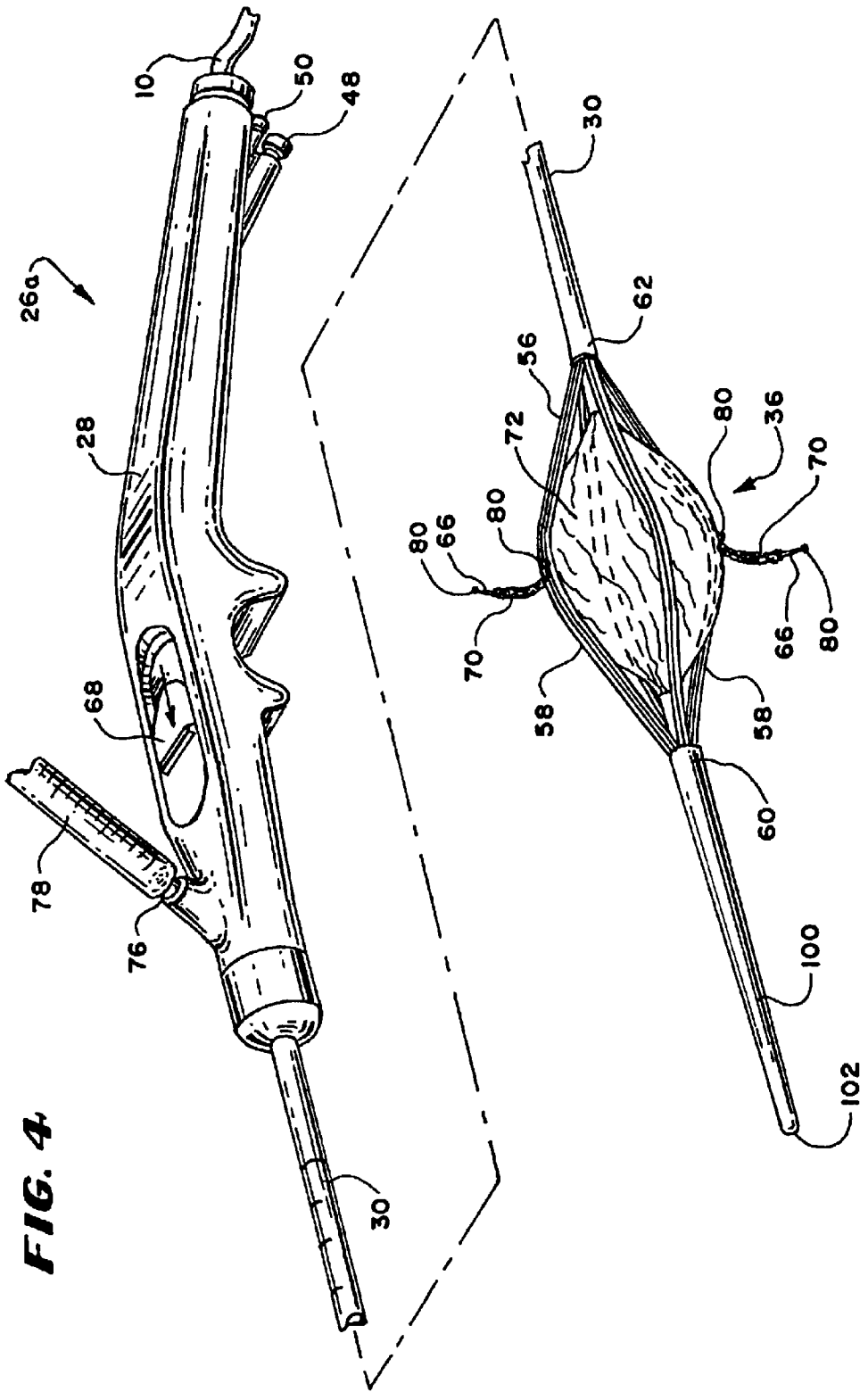
FIG. 4 is a perspective view, with portions broken away, of the device shown in FIG. 2, with the operative element shown in an expanded condition and the electrodes extended for use.

FIGS. 2 to 4 show a catheter-based device 26a for treating sphincter regions in the upper gastro-intestinal tract, and more particularly, the lower esophageal sphincter and adjoining cardia of the stomach to treat GERD. In the embodiment shown, the device 26a includes a flexible catheter tube 30 that carries a handle 28 at its proximal end. The distal end of the catheter tube 30 carries the operative element 36a.

In the illustrated embodiment, the operative element 36a comprises a three-dimensional basket 56. The basket 56 includes one or more spines 58, and typically includes from four to eight spines 58, which are assembled together by a distal hub 60 and a proximal base 62.

In the illustrated embodiment, an expandable structure 72 comprising a balloon is located within the basket 56. The balloon structure 72 can be made, e.g., from a Polyethylene Terephthalate (PET) material, or a polyamide (non-compliant) material, or a radiation cross-linked polyethylene (semi-compliant) material, or a latex material, or a silicone material, or a C-Flex (highly compliant) material.

The balloon structure 72 presents a normally, generally collapsed condition, as FIG. 2 shows. In this condition, the basket 56 is also normally collapsed about the balloon structure 72, presenting a low profile for deployment into the esophagus.

A catheter tube 30 includes an interior lumen, which communicates with the interior of the balloon structure 72. A fitting 76 (e.g., a syringe-activated check valve) is carried by the handle 28. The fitting 76 communicates with the lumen. The fitting 76 couples the lumen to a syringe 78 (see FIG. 3). The syringe 78 injects fluid under pressure through the lumen into the balloon structure 72, causing its expansion.

Figure 31:
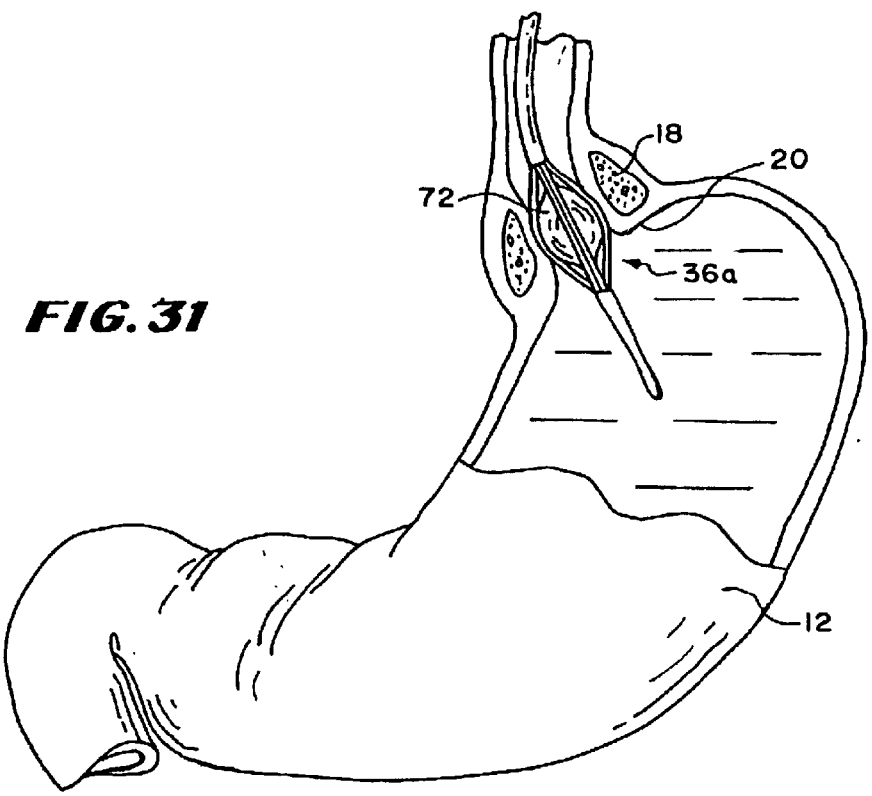
FIGS. 31 and 32 are side views, with portions broken away and in section, showing deployment of the treatment device shown in FIGS. 2 to 4 in the upper gastro-intestinal tract to treat dysfunction of the lower esophageal sphincter.

Expansion of the balloon structure 72 urges the basket 56 to open and expand (see FIG. 3). The force exerted by the balloon structure 72, when expanded, is sufficient to exert an opening or dilating force upon the tissue surrounding the basket 56 (see FIG. 31).

Each spine 58 carries an electrode 66 (see FIG. 4). In the illustrated embodiment, each electrode 66 is carried within the tubular spine 58 for sliding movement. Each electrode 66 slides from a retracted position, withdrawn in the spine 58 (shown in FIG. 3) and an extended position, extending outward from the spine 58 (see FIG. 4) through a hole in the spine 58. A push-pull lever 68 on the handle 28 is coupled by one or more interior wires to the sliding electrodes 66. The lever 68 controls movement electrodes between the retracted position (by pulling rearward on the lever 68) and the extended position (by pushing forward on the lever 68).

Figure 32:
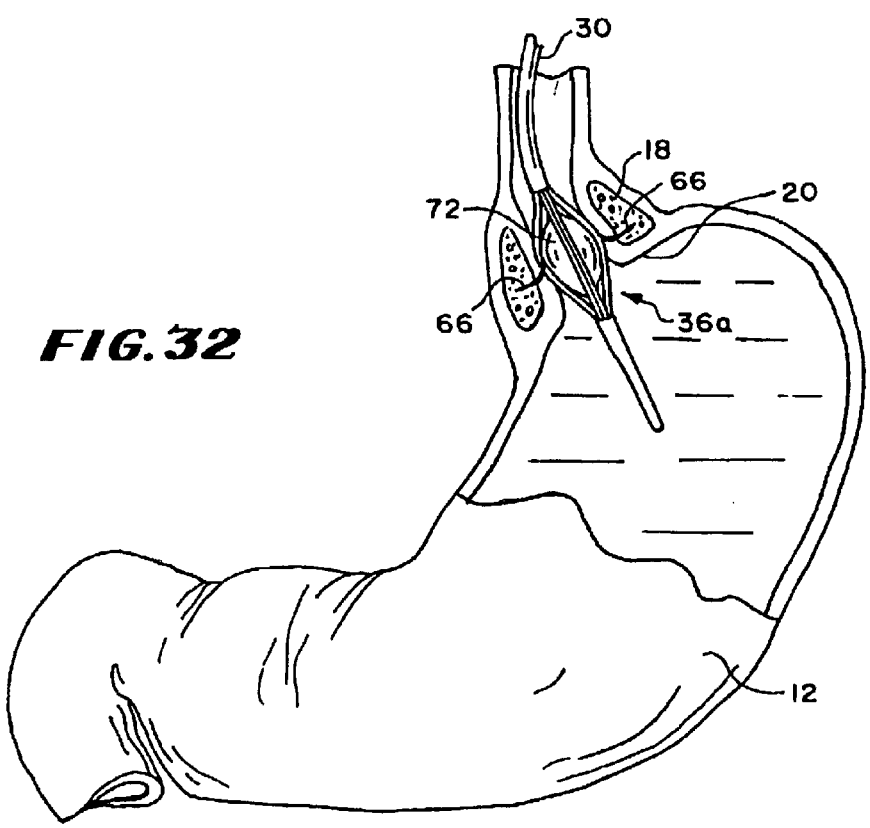

The electrodes 66 have sufficient distal sharpness and strength, when extended, to penetrate a desired depth into tissue the smooth muscle of the lower esophageal sphincter 18 or the cardia of the stomach 16 (see FIG. 32). The desired depth can range from about 4 mm to about 5 mm.

The electrodes 66 are formed of material that conducts radio frequency energy, e.g., nickel titanium, stainless steel, e.g., 304 stainless steel, or a combination of nickel titanium and stainless steel.

In the illustrated embodiment (see FIG. 4), an electrical insulating material 70 is coated about the proximal end of each electrode 66. When the distal end of the electrode 66 penetrating the smooth muscle of the esophageal sphincter 18 or cardia 20 transmits radio frequency energy, the material 70 insulates the mucosal surface of the esophagus 10 or cardia 20 from direct exposure to the radio frequency energy. Thermal damage to the mucosal surface is thereby avoided. The mucosal surface can also be actively cooled during application of radio frequency energy, to further protect the mucosal surface from thermal damage.

In the illustrated embodiment (see FIG. 4), at least one temperature sensor 80 is associated with each electrode. One temperature sensor 80 senses temperature conditions near the exposed distal end of the electrode 66, a second temperature sensor 80 is located on the corresponding spine 58, which rests against the mucosal surface when the balloon structure 72 is inflated.

The external fluid delivery apparatus 44 is coupled via tubing 12 (see FIG. 1) to connector 48 (see FIG. 4), to supply cooling liquid to the targeted tissue, e.g., through holes in the spines. The external aspirating apparatus 46 is coupled via tubing 14 (see FIG. 1) to connector 50 (see FIG. 4), to convey liquid from the targeted tissue site, e.g., through other holes in the spine or elsewhere on the basket 56. The controller 52 can govern the delivery of processing fluid and, if desired, the removal of aspirated material.

The controller 52 can condition the electrodes 66 to operate in a monopolar mode. In this mode, each electrode 66 serves as a transmitter of energy, and an indifferent patch electrode (described later) serves as a common return for all electrodes 66. Alternatively, the controller 52 can condition the electrodes 66 to operate in a bipolar mode. In this mode, one of the electrodes comprises the transmitter and an other electrode comprises the return for the transmitted energy. The bipolar electrode pairs can electrodes 66 on adjacent spines, or electrodes 66 spaced more widely apart on different spines.

Further details of the construction and use of the device 26a and other devices intended to be deployed to treat sphincter regions in the upper gastro-intestinal tract are disclosed in copending U.S. patent application Ser. No. 09/305,123, filed May 4, 1999, and entitled "Graphical User Interface for Association with an Electrode Structure Deployed in Contact with a Tissue Region," which is incorporated herein by reference.

B. For Treatment of Lower Gastro-Intestinal Tract

Figure 5:
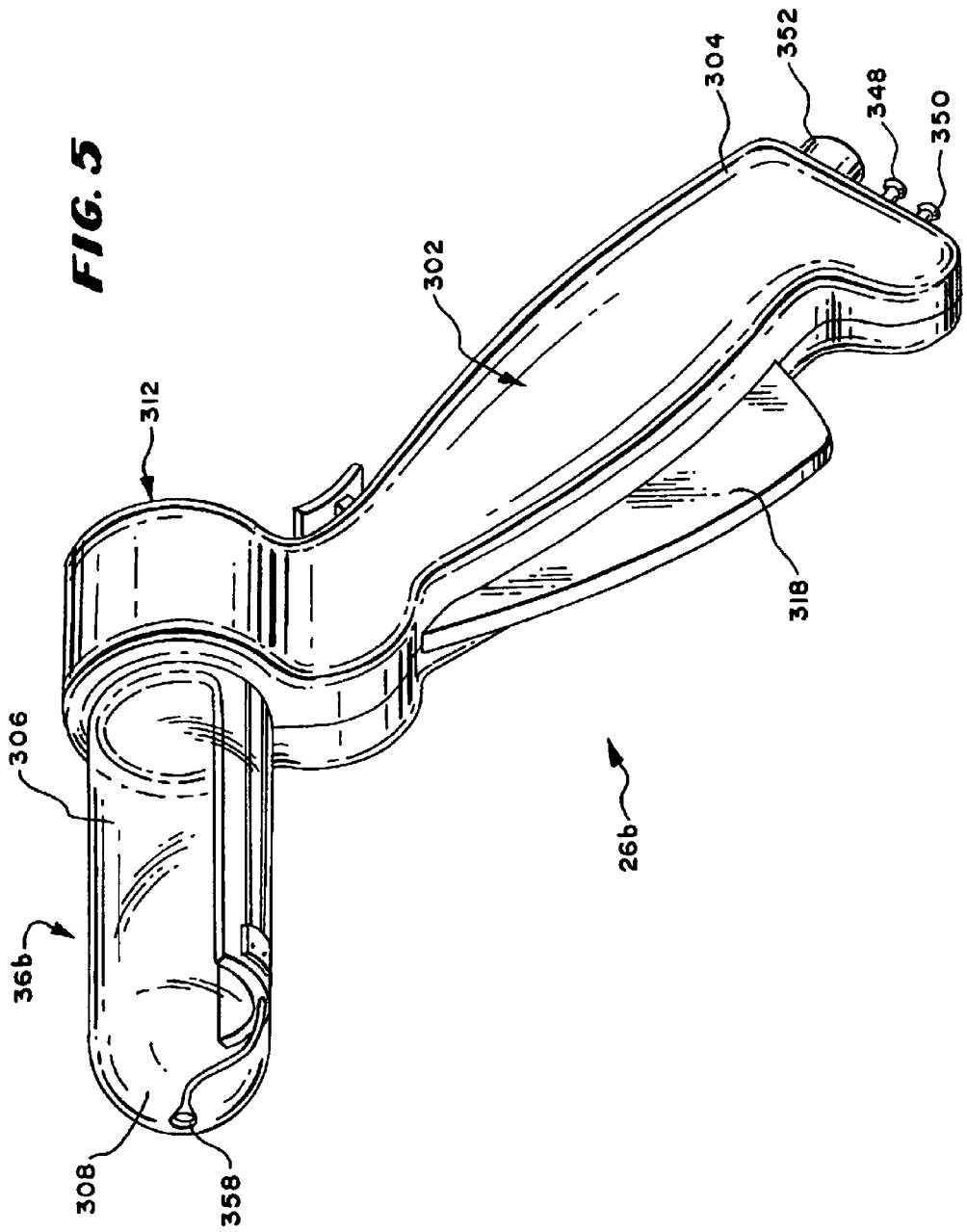
FIG. 5 is a perspective view of another type of treatment device usable in association with the system shown in FIG. 1 to treat tissue in the lower gastrointestinal tract, the treatment device having an array of electrodes shown in a retracted position.
Figure 6:
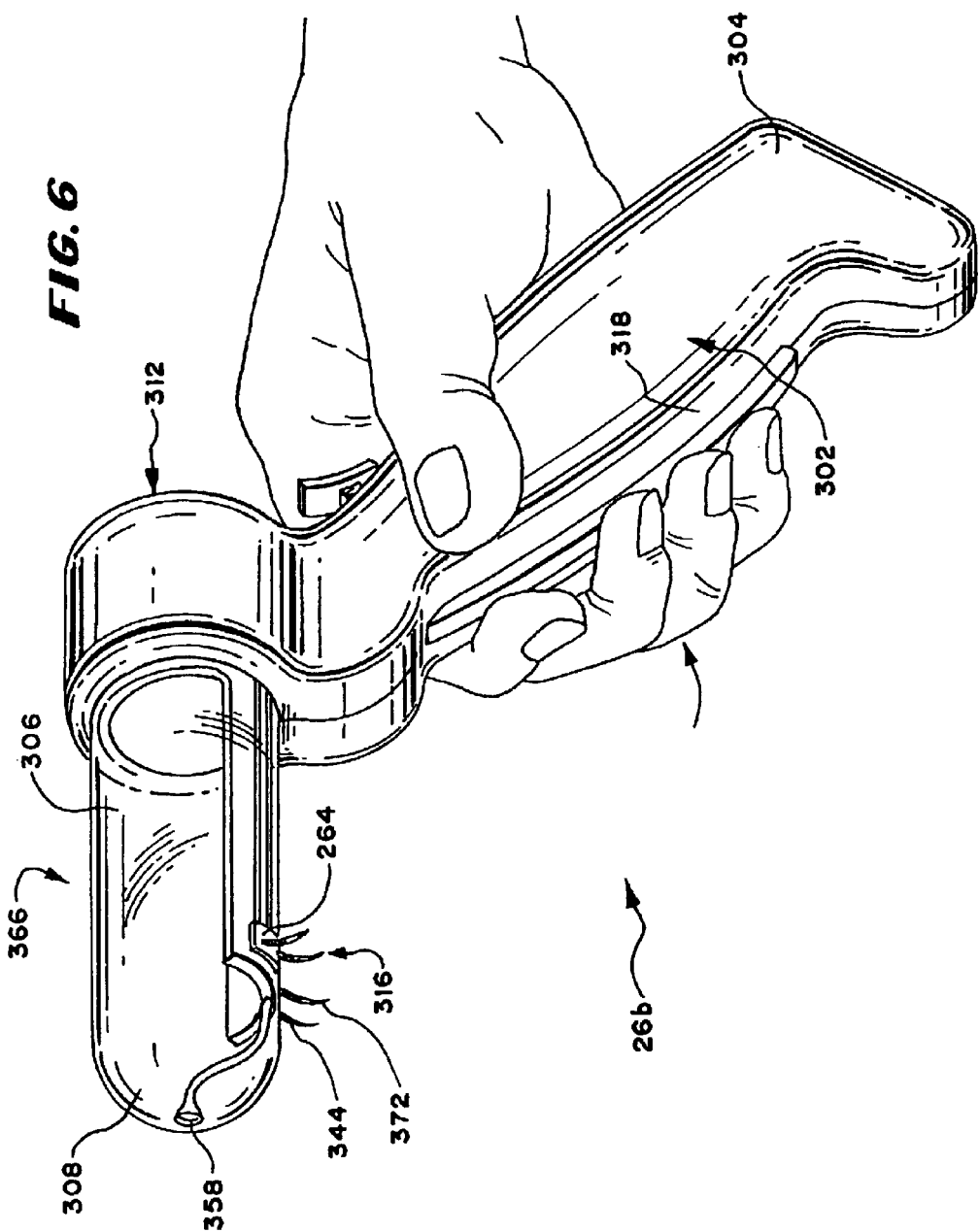
FIG. 6 is a perspective view of the device shown in FIG. 5, with the array of electrodes shown in their extended position.

FIGS. 5 and 6 show a representative embodiment for device 26b, which takes the form of a hand manipulated device 302 for treating sphincter regions in the lower gastrointestinal tract, and more particularly, the internal and/or external sphincter muscles in the anal canal to treat fecal incontinence. The device 302 includes a hand grip 304 that carries the operative element 36b.

In the illustrated embodiment, the operative element 36b takes the form of a hollow, tubular barrel 306 made from a transparent, molded plastic material. The barrel 306 terminates with a blunt, rounded distal end 308 to aid passage of the barrel 306 through the anal canal, without need for a separate introducer. The hand grip 304 includes a viewing port 312 for looking into the transparent, hollow interior of the barrel 306, to visualize surrounding tissue.

An array of needle electrodes 316 are movably contained in a side-by-side relationship along an arcuate segment of the barrel 306. In the illustrated embodiment, the needle electrodes 316 occupy an arc of about 67.5 degrees on the barrel 306. The needle electrodes 316 are mechanically linked to a finger-operated pull lever 318 on the hand grip 304. By operation of the pull lever 318, the distal ends of the needle electrodes 316 are moved between a retracted position (FIG. 5) and an extended position (FIG. 6). An electrical insulating material 344 is coated about the needle electrodes 316 (see FIG. 6), except for a prescribed region of the distal ends, where radio frequency energy is applied to tissue. The generator 38 is coupled via the cable 10 to a connector 352, to convey radio frequency energy to the electrodes 316.

Figure 33:
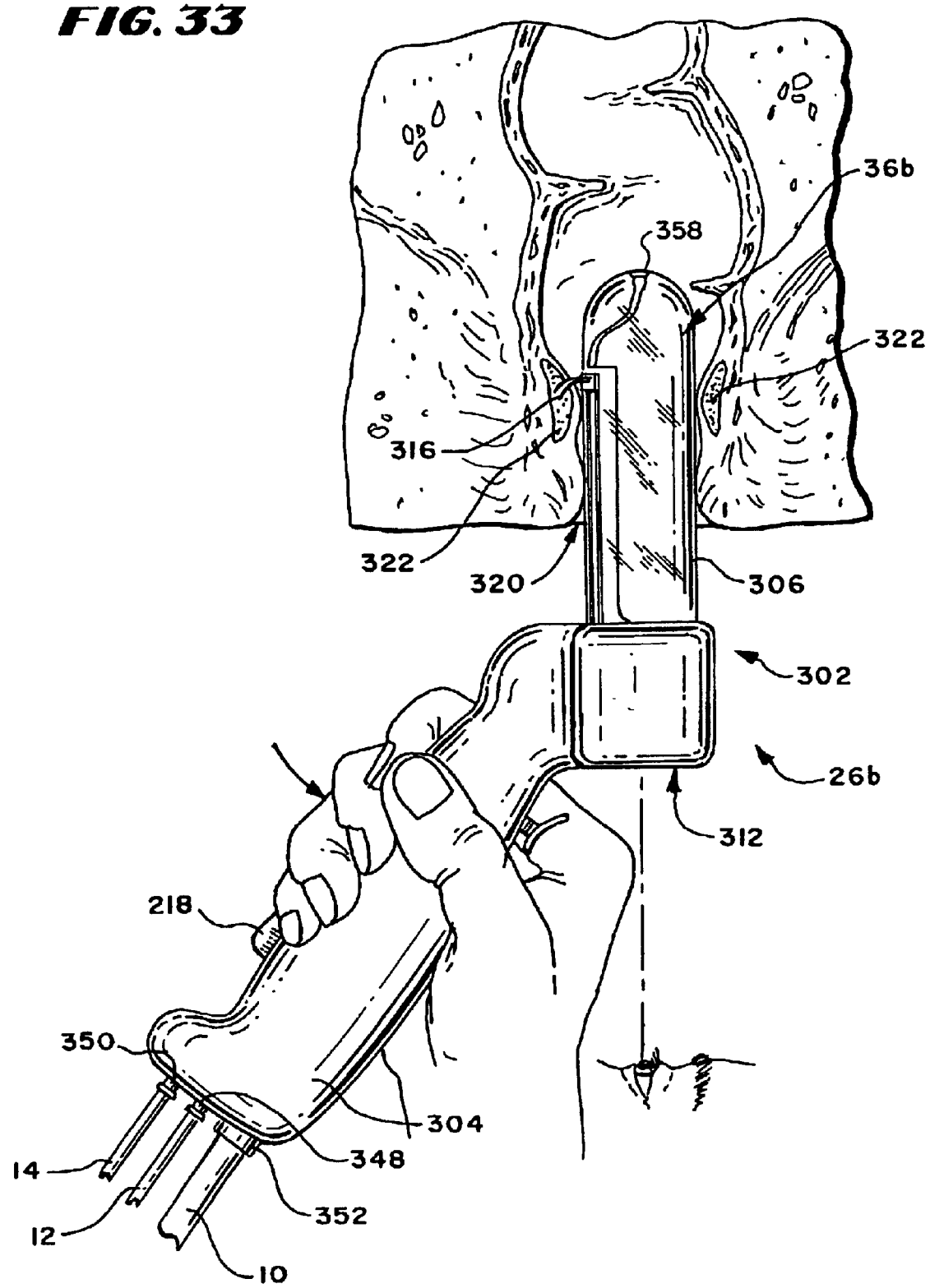
FIG. 33 is a side view, with portions broken away and in section, showing deployment of the treatment device shown in FIGS. 5 and 6 in the lower gastrointestinal tract to treat sphincter dysfunction in the anal canal.

In use (see FIG. 33), the physician grasps the hand grip 304 and guides the barrel 306 into the anal canal 320. The pull lever 318 is in the neutral position and not depressed, so the needle electrodes 316 occupy their normal retracted position. Looking through the viewing port 312, the physician visualizes the pectinate (dentate) line through the barrel 306. Looking through the barrel 306, the physician positions the distal ends of the needle electrodes 316 at a desired location above the pectinate (dentate) line. A fiberoptic can also be inserted into the barrel 306 to provide local illumination, or the physician can wear a headlamp for this purpose. Once the distal end of the barrel 306 is located at the targeted site, the physician depresses the pull lever 318 (as FIG. 33 shows). The needle electrodes 316 advance to their extended positions. The distal ends of the electrodes 316 pierce and pass through the mucosal tissue into the muscle tissue of the target sphincter muscle. In FIG. 33, the distal end of the electrodes 316 are shown penetrating the involuntary, internal sphincter muscle 322. The physician commands the controller 52 to apply radio frequency energy through the needle electrodes 316. The energy can be applied simultaneously by all electrodes 316, or in any desired sequence.

The external fluid delivery apparatus 44 is coupled via tubing 12 to a connector 348 to convey a cooling liquid, e.g., through holes in the barrel 306, to contact tissue at a localized position surrounding the electrodes 316. The external aspirating apparatus 46 is coupled via tubing 14 to a connector 350 to convey liquid from the targeted tissue site, e.g., through an aspiration port 358 in the distal end 308 of the barrel 306 (see FIGS. 5 and 6).

The barrel 306 (see FIG. 6) also preferably carries temperature sensor 364, one of which is associated with each needle electrode 316. The sensors 364 sense tissue temperature conditions in the region adjacent to each needle electrode 316. Preferably, the distal end of each needle electrode 316 also carries a temperature sensor 372 (see FIG. 6).

Further details of the construction and use of the device 26b and other devices that can be deployed to treat sphincter regions in the lower gastro-intestinal tract are disclosed in copending U.S. patent application Ser. No. 09/305,123, filed Apr. 21, 2000, and entitled "Systems and Methods for Treating Dysfunctions in the Intestines and Rectum," which is incorporated herein by reference.

III. Monitoring and Controlling Use of the Devices

Each device 26a and 26b preferably forms an integrated construction intended for a single use and subsequent disposal as a unit. To protect patients from the potential adverse consequences occasioned by multiple use, which include disease transmission, or material stress and instability, or decreased or unpredictable performance, the controller 52 includes a module 64 that controls use of each device 26a and 26b.

In the illustrated embodiment (see FIG. 7), each device 26a/26b is supplied as part of a kit 200 that includes, together with the device 26, a usage key card 202. The kit 200 packages the device 26a/26b and usage key card 202 as a unitary, single use item in a sterile fashion within peripherally sealed sheets of plastic film material that are torn or peeled away at the instance of use.

The presence of the device 26a/26b and user key card 200 packaged together in the kit 200 verifies to the physician or user that device 26a/26b is sterile and has not been subjected to prior use. The physician or user is thereby assured that the device 26a/26b meets established performance and sterility specifications. No unused device 26a/26b is supplied in the kit 200 without a usage key card 202, and vice versa.

The usage key card 202 for each device 26a/26b incorporates a storage medium 204 that is readable by the module 64. The storage medium 204 contains information that enables at least three use control and monitoring functions.

The first use control and monitoring function of the usage key card 202 occurs prior to use of the selected device 26a/26b in association with the generator 38. To enable use of the generator 38 in association with the selected device 26a/26b, the physician must first present the usage key card 202 for reading by the module 64. To enable use of the selected device 26a/26b, the controller 52 must then find that the usage key card 202 meets the criteria necessary for its registration by the controller 52. The criteria are designed to indicate the absence of a prior use, either in absolute terms or in terms of a period of use outside a predetermined time period. If the criteria are not met, the controller 52 will not register the usage key card 202, and the controller 52 will also not enable use of the generator 38 in association with the selected device 26a/26b. Further details of the registration function of the controller 52 will be described later.

The second use control and monitoring function occurs if the criteria are met and registration of the usage key card 202 occurs. The second use control and monitoring function identifies the particular type of device 26a/26b that has been selected for use. The second use and control function conditions the controller 52 to implement only those control algorithms and operator interface displays particular to the selected device 26a/26b. Further details of this control aspect will be described later.

The third use control and monitoring function of the usage key card 202 occurs during permitted use of the selected device 26//26b in association with the generator 38. During permitted use, the storage medium 204 of the usage key card 202 remains in the module 64 and receives, via the module 64, data generated by the controller 52 recording operating parameters and performance of the selected device 26a/26b. The storage medium 204 of the usage key card 202 retains and organizes the data for further off-line storage and processing. Further details of the data retention function will be described later.

The usage key card 202 can be variously configured. In the illustrated embodiment (see FIG. 8), the usage key card 202 comprises a computer-readable storage medium 204 housed within a conventional 3.5 inch floppy disk 206. In this arrangement, the module 64 comprises a conventional floppy disk drive 208 (see FIG. 9) capable of reading data from and downloading data to the storage medium 204 of the disk 206.

Alternatively, the usage key card 202 can take the form of a PC card, flash memory device, or magnetic card. In these alternative embodiments, the module 64 comprises a data reading and writing device compatible with the storage medium of the card 202.

Figure 8:
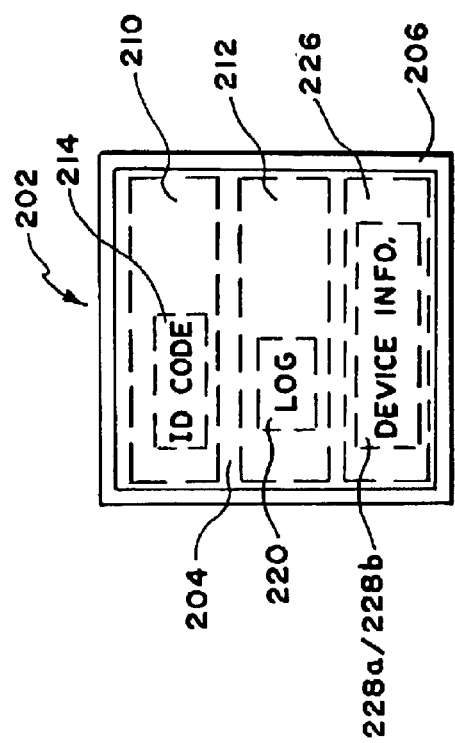
FIG. 8 is an enlarged, mainly schematic view of the usage key card shown in FIG. 7, embodied as a floppy disk, and also showing the pre-formatted files it contains.

As FIG. 8 shows, the storage medium 204 of the usage key card 202 contains at least three pre-formatted files 210, 226, and 212. The first file 210 contains a unique identification code 214 capable of being read by the module 64 and registered by the controller 52. The second file 226 contains another identification code that specifies the particular type of device 26a/26b that has been selected, which thereby indicates the desired treatment protocol that has been selected. The third file 212 is formatted to receive and retain operational and performance data generated by the controller 52 to create from it a procedure log 220.

The identification code 214 contained in the first file 210 is created to be unique to the particular usage key card 202. That is, each usage key card 202 contains its own unique identification code 214. No two usage key cards share the same identification code 214. The unique identification code 214 can comprise, e.g., a serial number uniquely assigned to the particular device 26a/26b found in the kit 200, or any other unique code that is not repeated for any other usage key card 202. The code 214 itself can comprise letters, numbers, or combinations thereof.

Figure 9:
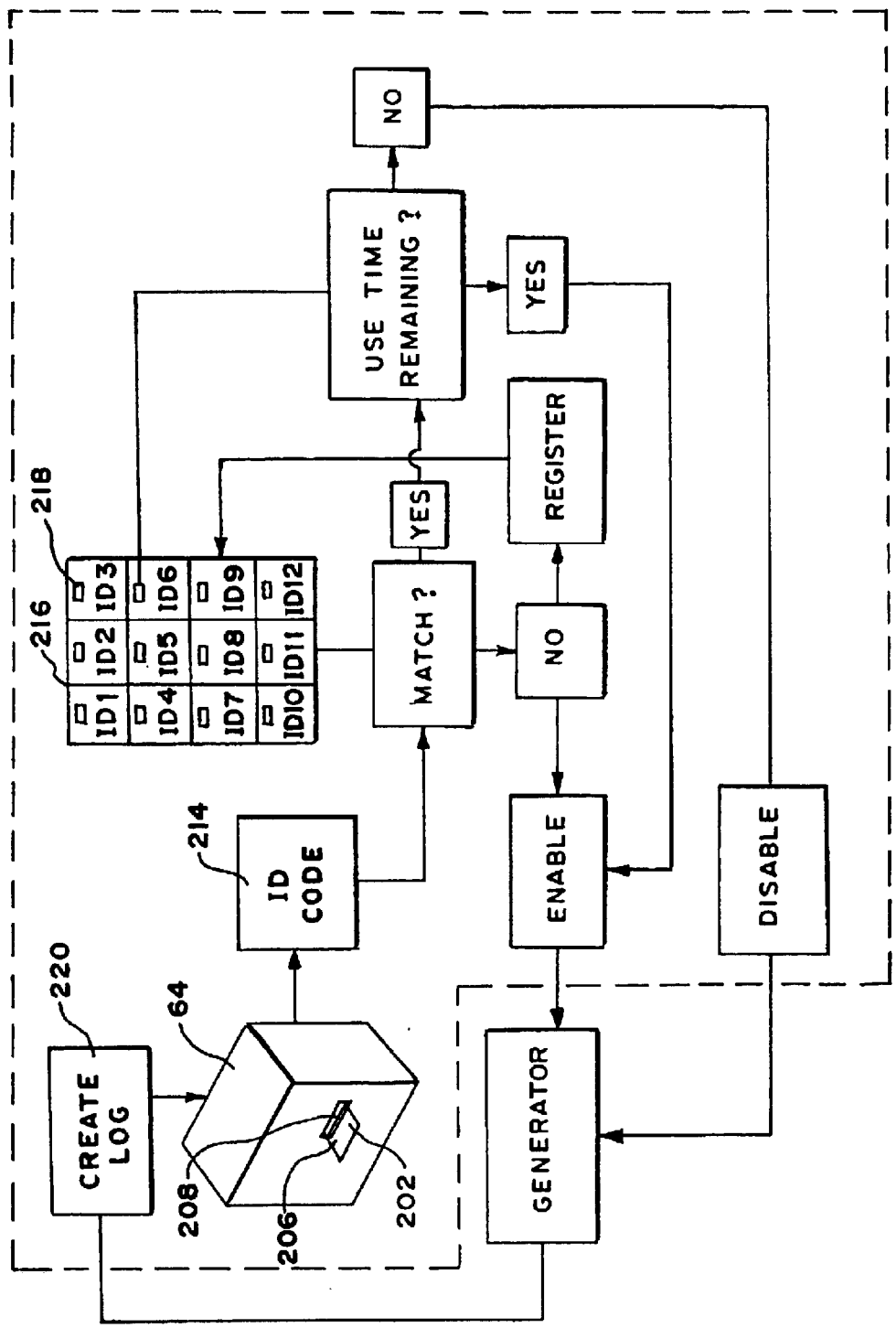
FIG. 9 is a schematic view of a controller, which the system shown in FIG. 1 incorporates, showing the pre-programmed rules by which information contained on the usage key card shown in FIGS. 7 and 8 is read and processed.

As FIG. 9 shows, the module 64 reads the identification code 214 off the usage key card 202 for input to the controller 52. This identification code will be called the "instant identification code."

Following pre-programmed rules, the controller 54 constructs and maintains in non-volatile memory a use table 216. The use table 216 contains all prior identification codes that meet the criteria to be registered by the controller 52. These identification codes will be called the "registered identification codes."

Following pre-programmed rules, the controller 52 compares the instant identification code 214 to all registered identification codes contained in the table 216. In the absence of a match between the instant identification code and any registered identification code, the controller 52 updates the table, i.e., the controller registers the instant identification code by adding it to the table 216. Upon registering the usage key card 202, the controller 52 also enables use of generator 38 in association with the selected device 26a/26b.

The presence of a match between the instant identification code and any registered identification code indicates the usage key card 202 has been previously read by the module 64, which reflects a prior use of the selected device 26a/26b or another device not packaged with the card 202. In this circumstance, the controller 52 does not add the duplicate identification code to the table 216 and does not enable use of the generator 38 in association with any device 26. Preferably, the controller 52 outputs to the GUI 54 notice of prior use.

In an alternative arrangement, the controller 52 maintains for each registered identification code in the table 216 a time record 218. The time record 218 contains a value reflecting the period of time during which energy was applied by the generator 38 during the previous permitted use. In this embodiment, when a match occurs between the instant identification code and a registered identification code, the controller 52 ascertains whether the time period of previous use contained in the record 218 is less than a prescribed maximum time period, e.g., 45 minutes. If so, the controller 52 enables a subsequent operation of the generator 38 in association with the device 26, but only for the time period remaining. The controller 52 updates the time record 218 as further use occurs. The controller 52 preferably outputs to the GUI the time period of permitted use remaining.

If the controller 52 ascertains that the time period of previous use equals or exceeds the prescribed maximum time period, the controller 52 does not enable use of the generator 38. Preferably, the controller 52 outputs to the GUI notice of prior use.

As FIG. 8 shows, the second file 226 contained in the storage medium 204 of the usage key card 202 is created to uniquely identify the particular configuration and intended use of the device 26a or 26b that has been selected. The file 226 contains a first identification code 228a if device 26a has been selected. The file 226 contains a second identification code 228b if device 26b has been selected. The codes 228a and 228b can comprise letters, numbers, or combinations thereof.

The codes 228a/228b can identify the type of device 26a/26b in terms of its operational characteristics, the inclusion of temperature sensing, and reuse criteria (e.g., no reuse after a single use, or multiple uses permitted up a prescribed maximum number of uses, or multiple uses permitted up to a maximum time period of use, or multiple uses permitted up to a maximum application of RF energy). In one arrangement, the controller 52 can compare the device characteristics with the operational characteristics of the controller 52 and generator 38, and disable operation of the device 26 should the characteristics of the device 26 be incompatible with the characteristics of the controller 52 and/or generator 38.

Once the criteria for registration of the usage key card 202 are met, the module 64 reads the identification code 228a or 228b off the usage key card 202 for input to the controller 52. Following pre-programmed rules, the controller 54 implements only those particular control algorithms intended for the selected device 26a/26b. As will be described in greater detail later, the controller 52 can, in response to reading the identification code 228a or 228b also condition the GUI 54 to display the desired images and data formats, which change depending upon the treatment procedure using the selected device 26a/26b (e.g, treatment of GERD using the device 26a or the treatment of fecal incontinence using the device 26b). Thus, the system 10 accommodates different control schemes and different graphical interfaces in support of different treatment protocols.

Figure 10:
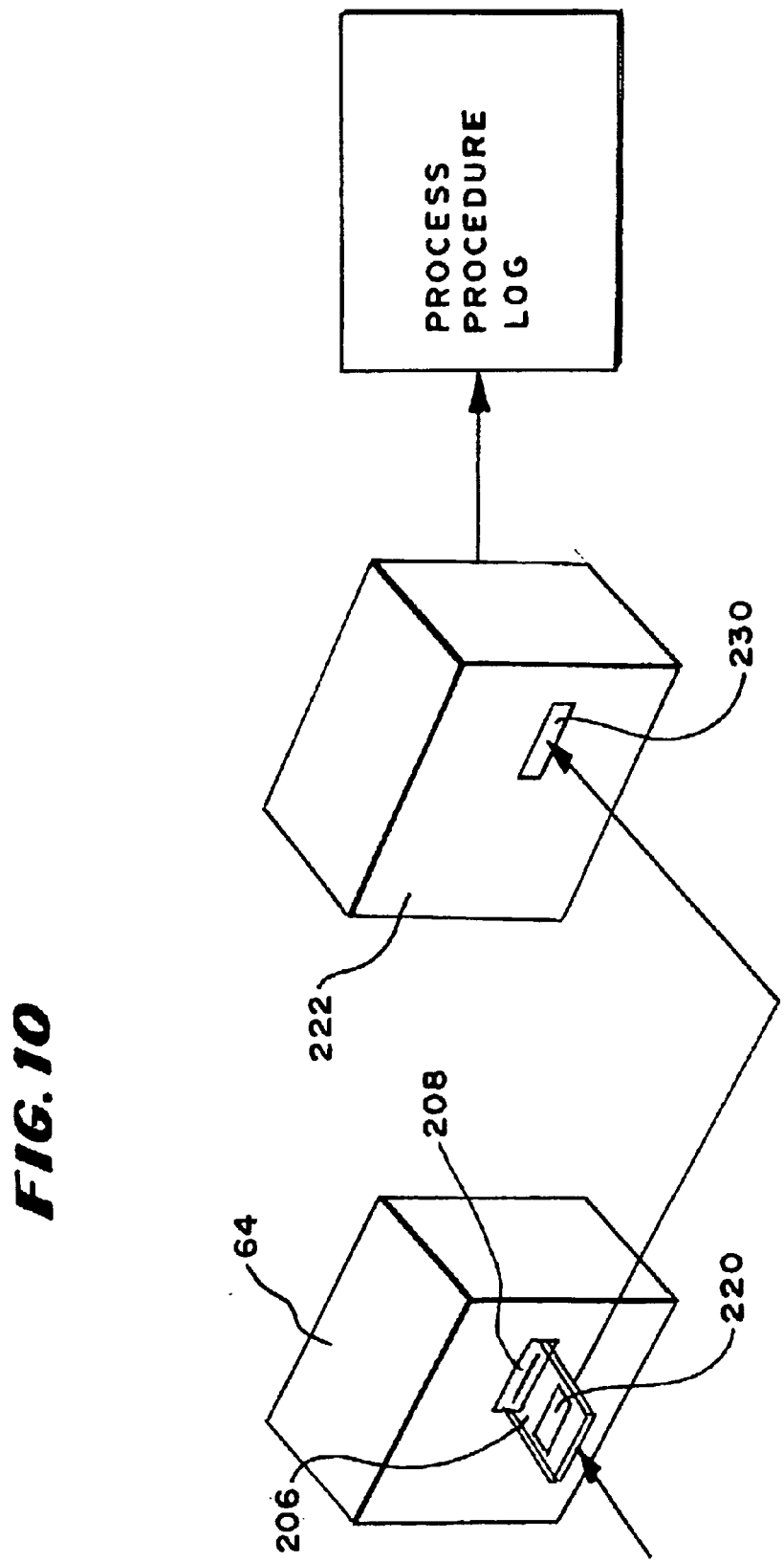
FIG. 10 is a schematic view of another processing device that reads information from the usage key card shown in FIG. 7, for further processing.

As FIG. 8 shows, the third file 212 contained on the storage medium 204 of the usage key card 202 is formatted to receive, via the module 64, data that is generated by the controller 52 during permitted use of the selected device 26a/26b in association with the generator 38. The file 212 retains the data in a formatted array according to pre-programmed rules to create a procedure log 220 (see FIG. 10).

The content of the formatted log 220 can vary. For example, the log 220 can document, by date of treatment and number of treatments, the coagulation level (i.e., the depth at which the electrodes are inserted), the time duration of energy application, the magnitude of energy delivered by each electrode, and the coolant flow rate. The procedure log 220 can also record at pre-established intervals (e.g., every 5 seconds) the temperatures of the electrodes and surrounding tissue, along other parameters, e.g., sensed impedance and power delivered by each electrode.

The procedure log 220 preferably records these values in a pre-formatted data base format, to enable import of the values as data base items for storage, processing, and retrieval by an off-line data processing device 222 having a compatible data base processing application. The off-line data processing device 222 reads processing log data from the usage key card 202 (via a floppy disk drive 230 or otherwise compatible reading device).

The device 222 can process the data in various ways according to the rules of the data processing application. The device 222 can, e.g., create a print-formatted record of the procedure log 220 for printing in a hard copy version. The device 222 can also, e.g., process the procedure logs for multiple devices and patients, to create historical patient treatment records, patient reimbursement records, and the like for storage or retrieval. The device 222 thereby makes possible the establishment and maintenance of an archival patient data base by processing individual procedure logs.

Figure 7:
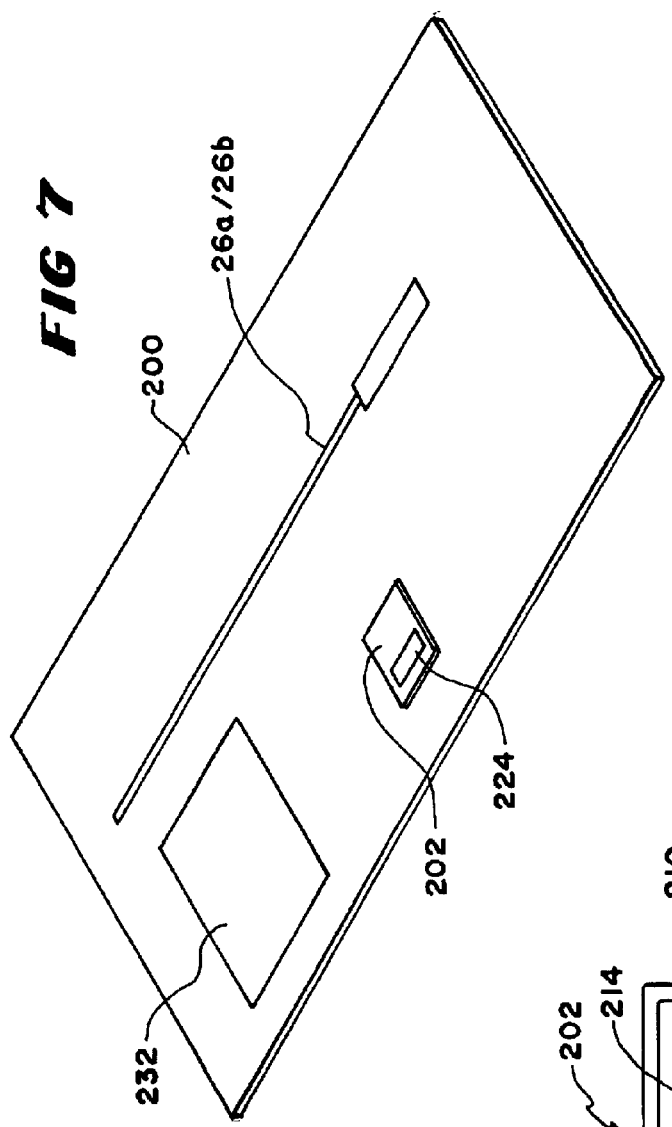
FIG. 7 is a perspective view of a kit containing a device, such as shown in FIG. 2 or 5, and a usage key card.

As FIG. 7 shows, the kit 200 can also include a label 224 that is pre-applied or that can be applied by the physician to the usage key card 202. The label 224 receives manually transcribed, visually readable information pertaining to the usage key card 202, e.g., the name of the patient being treated by the device 26, the date of treatment, and the like. In this way, usage key cards 202 can itself be physically stored and indexed.

As FIG. 7 also shows, the kit 200 can also include instructions 232 for using the usage key card 202 in the fashion described. For example, the instructions 232 can instruct the physician as to the need for having the usage key card 202 read by the module 64, in order to enable use of the device 26 in association with the generator 38. The instructions 232 can also instruct the physician regarding the content of the procedure log and the subsequent off-line processing options that are available.

Further details regarding the usage key card 202 can be found in co-pending U.S. patent application Ser. No. 09/574,704, filed May 18, 2000, and entitled "Graphical User Interface for Monitoring and Controlling Use of Medical Devices," which is incorporated herein by reference.

IV. System Operation

In the illustrated embodiment (see FIGS. 11A and 11B), the radio frequency generator 38, the controller 52 with I/O device 54, and the fluid delivery apparatus 44 (e.g., for the delivery of cooling liquid) are integrated within a single housing 400. The I/O device 54 includes input connectors 402, 404, and 406. The connector 402 accepts an electrical connector 408, to which the selected treatment device 26a/26b is electrically coupled for use. The connector 404 accepts an electrical connector 410 coupled to a patch electrode 412 (for monopolar operation). The connector 406 accepts an pneumatic connector 414 coupled to a conventional foot pedal 416, when, when depressed, causes the delivery of radio frequency energy to the electrodes 66 on the device 26. These connectors 402, 404, and 406 couple these external devices to the controller 52.

The I/O device 54 also couples the controller 52 to an array of membrane keypads 422 and other indicator lights on the housing 400, for entering and indicating parameters governing the operation of the controller 52.

Figure 12:
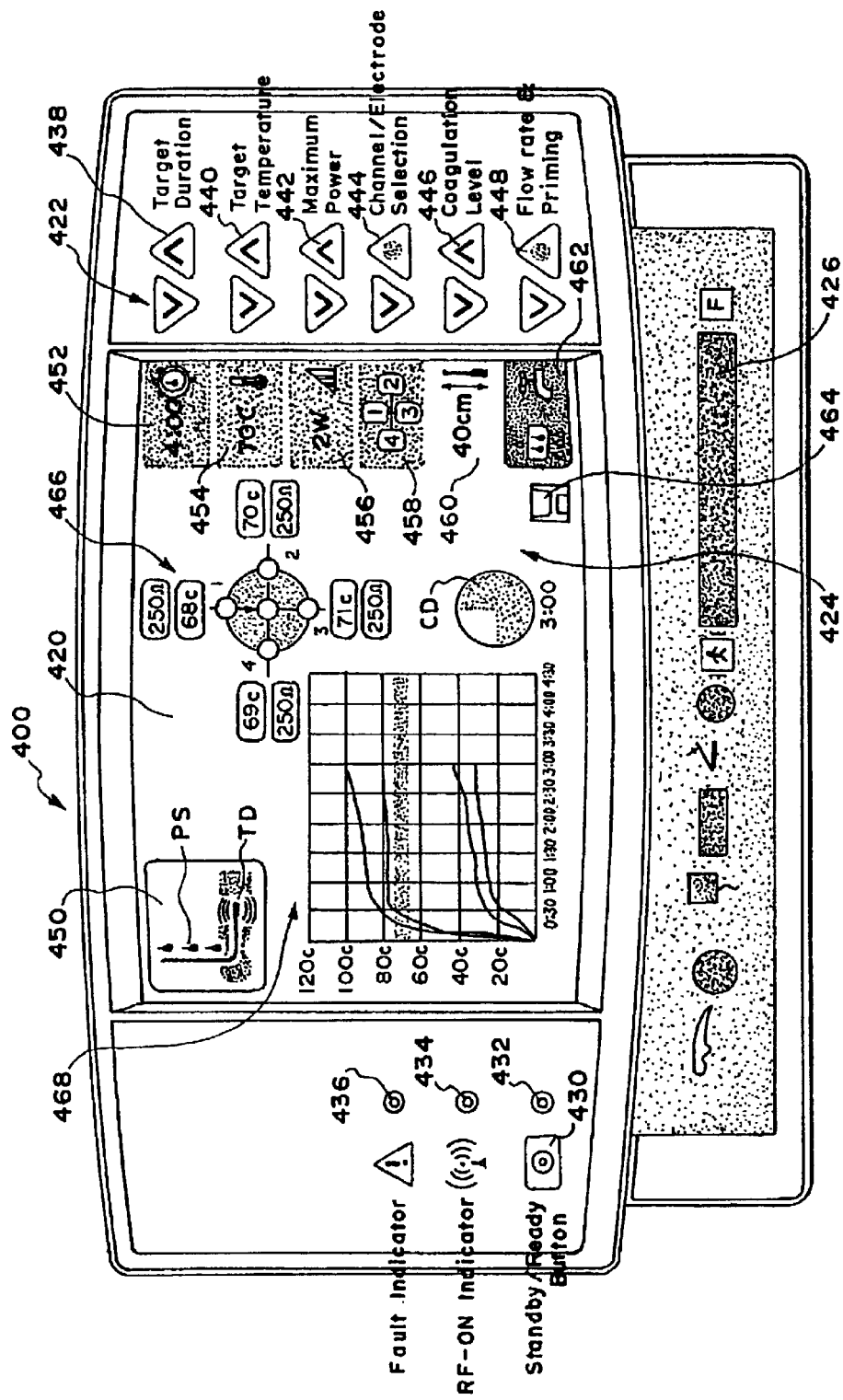
FIG. 12 is a front view of the device shown in FIGS. 11A and 11B showing the components of the graphical user interface.

In the illustrated embodiment, as shown in FIG. 12, the keypads 422 and indicators include:

1. Standby/Ready Button 430, which allows switching from one mode of operation to another, as will be described later.
2. Standby/Ready Indicator 432, which displays a green light after the device 400 passes a self test upon start up.
3. RF On Indicator 434, which displays a blue light when radio frequency energy is being delivered.
4. Fault Indicator 436, which displays a red light when an internal error has been detected. No radio frequency energy can be delivered when the Fault Indicator 436 is illuminated.
5. Target Duration Keys 438, which allow increases and decreases in the target power duration at the start or during the course of a procedure.

6. Target Temperature Keys 440, which allow increases and decreases in the target temperature at the start or during the course of a procedure.
7. Maximum Power Keys 442, which allow increases and decreases in the maximum power setting at the start or during the course of a procedure.
8. Channel Selection Keys 444, which allow selection of any or all power channels.
9. Coagulation Level Keys 446, which manually increases and decreases the magnitude of the indicated depth of insertion of the electrodes of the device 26a within the esophagus. This depth is determined, e.g., by visually gauging the measured markings along the length of the catheter tube of the treatment device 26a. Alternatively, the coagulation level can be automatically detected by, e.g., placing optical, mechanical, or magnetic sensors on an associated mouth piece inserted into the esophagus, which detect and differentiate among the measured markings along the catheter tube of the treatment device 26a to read the magnitude of the depth of insertion.
10. Flow Rate and Priming Keys 448, which allow for selection of three internally calibrated flow rates, low (e.g., 15 ml/min), medium (e.g., 30 ml/min), and high (e.g., 45 ml/min). Pressing and holding the "Up" key activates the pump at a high flow rate for priming, overruling the other flow rates until the "Up" key is released.

Figure 11A:
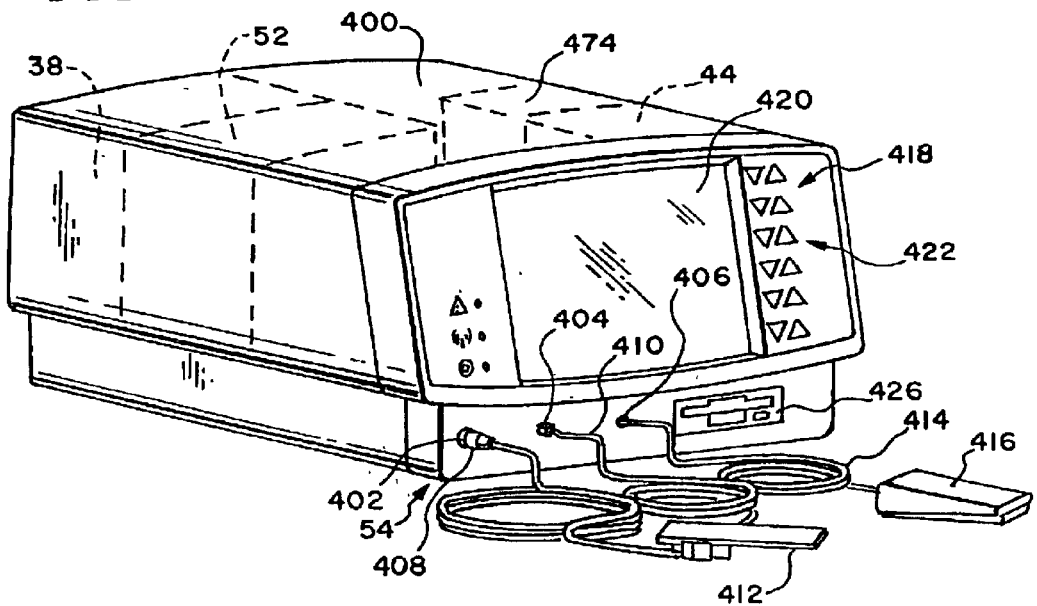
FIGS. 11A and 11B are, respectively, left and right perspective views of one embodiment of an integrated device incorporating features of the system shown in FIG. 1 and usable with either treatment device shown in FIG. 2 or 5 for treating body sphincters and adjoining tissue regions, and also having a graphical user interface.
Figure 11B:
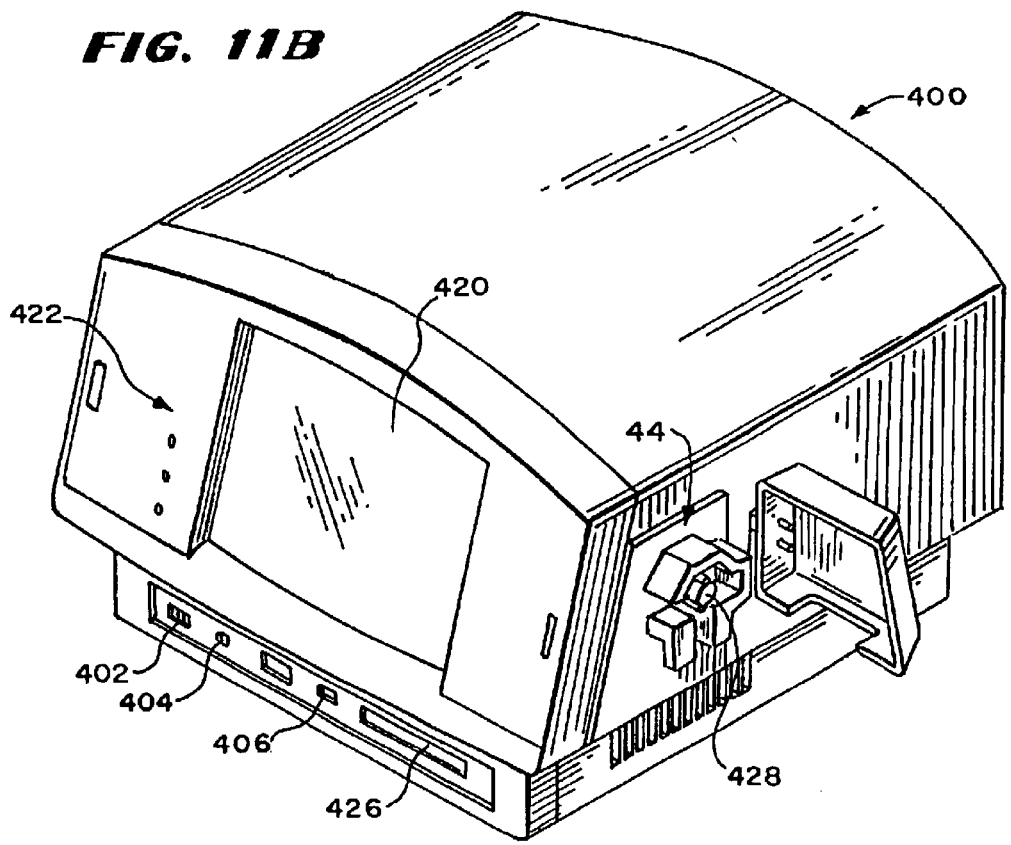

The I/O device 54 also couples the controller 52 to a display microprocessor 474 (see FIG. 11A). In the illustrated embodiment, the microprocessor 474 comprises, e.g., a dedicated Pentium1□based central processing unit. The controller 52 transmits data to the microprocessor 474, and the microprocessor 474 acknowledges correct receipt of the data and formats the data for meaningful display to the physician. In the illustrated embodiment, the dedicated display microprocessor 474 exerts no control over the controller 52.

In the illustrated embodiment, the controller 52 comprises an 68HC11 processor having an imbedded operating system. Alternatively, the controller 52 can comprise another style of processor, and the operating system can reside as process software on a hard drive coupled to the CPU, which is down loaded to the CPU during system initialization and startup.

The display microprocessor 474 is coupled to a graphics display monitor 420 in the housing 400. The controller 52 implements through the display microprocessor 474 the graphical user interface, or GUI, which is displayed on the display monitor 420.

The GUI can be realized, e.g., as a VISUAL BASICJ language program implemented by the microprocessor 474 using the MS WINDOWSJ or NT application and the standard WINDOWS 32 API controls, e.g., as provided by the WINDOWSJ Development Kit, along with conventional graphics software disclosed in public literature.

The display microprocessor 474 is also itself coupled to the floppy disk drive 426, previously described as floppy disk module 208 (FIG. 9). The display microprocessor 474 can also be coupled to a keyboard, printer, and include one or more parallel port links and one or more conventional serial RS-232C port links or Ethernet™ communication links.

The graphics display monitor 420 can comprise an active matrix LCD display screen located between the membrane keypads 422 and other indicators on the front panel. The GUI 424 is implemented by showing on the monitor 420 basic screen displays.

In the illustrated embodiment, these displays signify four different operating modes: Start-Up, Standby, Ready, RF-On, and Pause.

A. Start-up: Monitoring and Controlling Reuse

Figure 13:
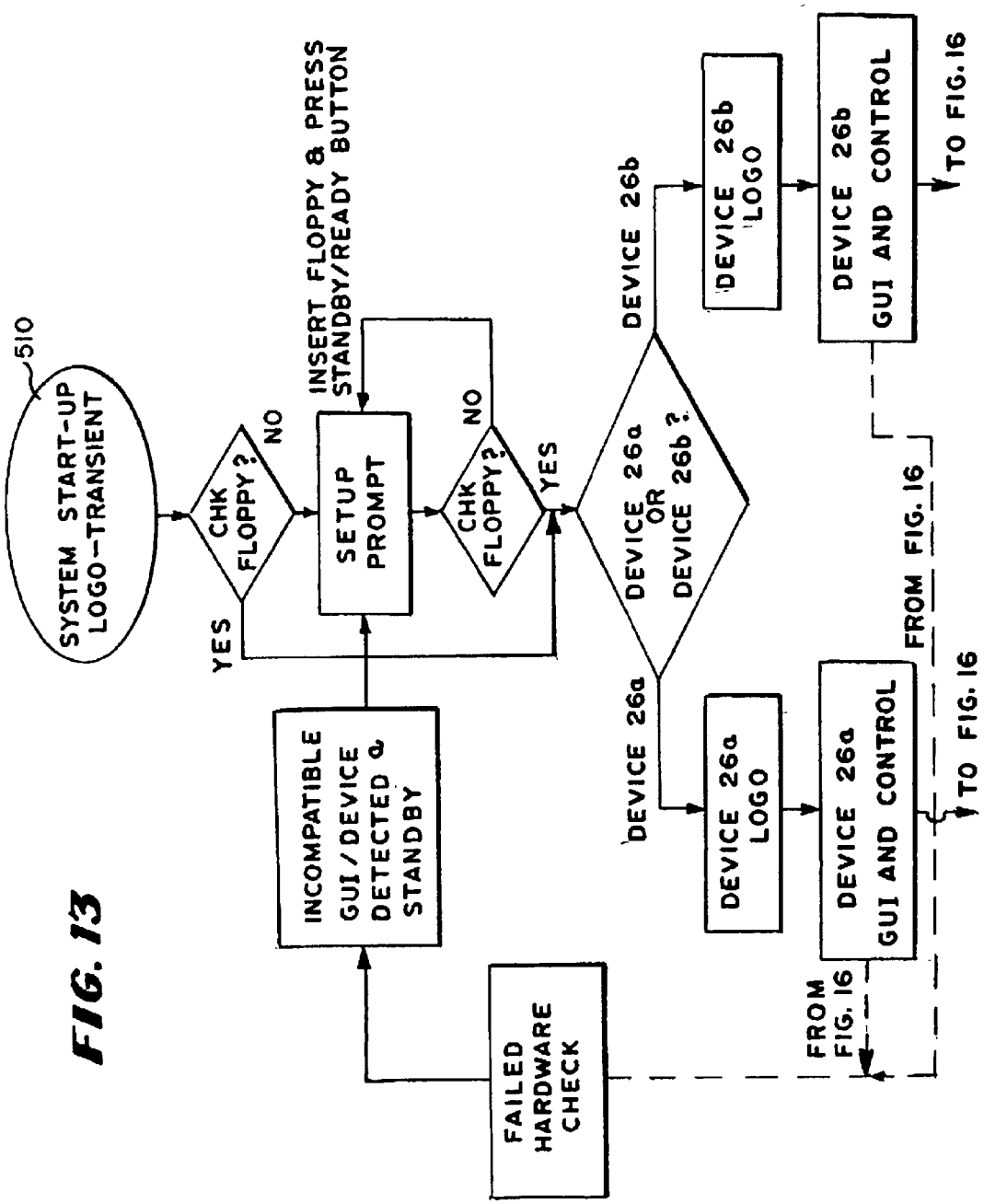
FIG. 13 is a flow chart showing further details of the pre-programmed rules by which information contained on the usage key card shown in FIGS. 7 and 8 is read and processed to set up use of a selected treatment device with the device shown in FIGS. 11A, 11B, and 12.

Upon boot-up of the CPU (see FIG. 13), the operating system implements the START-UP function 510 for the GUI 424. The GUI 424 displays an appropriate start-up logo and title image (not shown), while the controller 52 performs a self-test.

Upon completion of the START-UP function (see FIG. 13), the controller 52 conducts a CHECK function 512. The function 512 checks for the presence of a usage key card 202 in the floppy disk drive 426. As before described, a valid usage key card 202 is a prerequisite for using a given treatment device 26.

Figure 14:
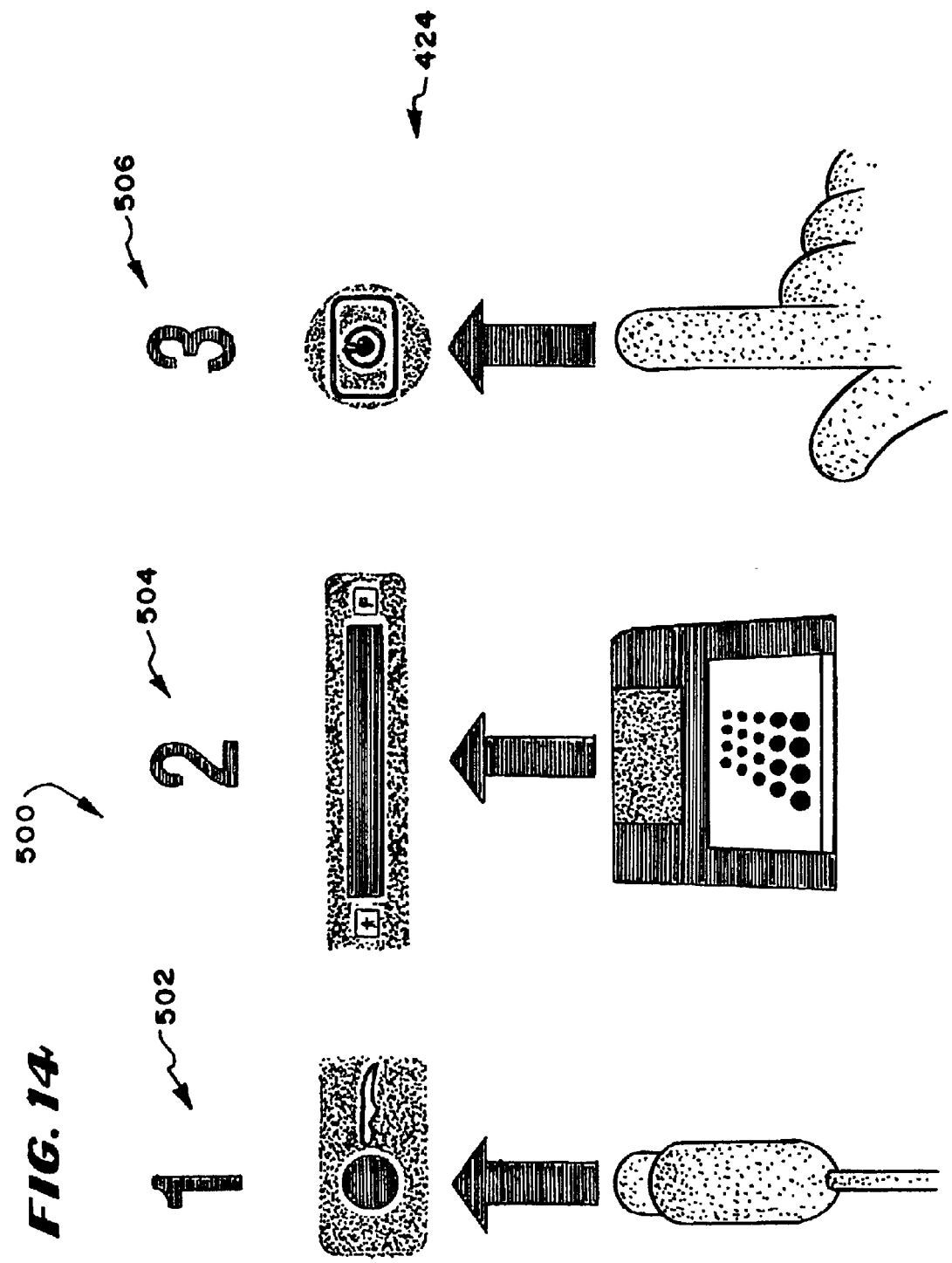
FIG. 14 is a representative SETUP display that can be implemented by the graphical user interface of the device shown in FIGS. 11A, 11B, and 12, following the pre-programmed rules shown in FIG. 13, as part of monitoring and controlling the use of a selected treatment device.

The absence of a usage key card 202 causes the controller 52 to command the display microprocessor 474 to generate a SETUP prompt 500 on the graphics display monitor 420. FIG. 14 shows a representative SETUP prompt 500. When graphically implemented, as shown in FIG. 14, the SETUP prompt 500 leads the operator in a step-wise fashion through the tasks required to enable use of the generator 38. A first graphic field displays one or more icons and/or alpha-numeric indicia 502 that prompt the operator to connect the electrical connector 42 of the treatment device 26 to the connector cable 408. A second graphic field displays one or more icons and/or alpha-numeric indicia 504 that prompt the operator to insert a valid user key card 202 (i.e., floppy disk). A third graphic field displays one or more icons and/or alpha-numeric indicia 506 that prompt the user to select the standby-ready button 430 on the housing 400 (see FIG. 12).

With the selected treatment device 26a/26b connected and a user key card 202 inserted in the floppy disk drive 426, and the standby-ready button 430 pressed, the controller 52 reads the device identification code 228a or 228b on the user key card 202. In this way, the controller 52 ascertains which device 26a or 26b has been selected for use. Based upon this input, the controller 52 proceeds to execute the preprogrammed control and graphical GUI command functions for the device 26a and 26b that the user key card 202 indicates has been selected.

If the identification code 228a is registered, the GUI 424 displays an appropriate start-up logo and title image for the device 26a. Likewise, if the identification code 228b is registered, the GUI 424 displays an appropriate start-up logo and title image for the device 26b.

Figure 15:
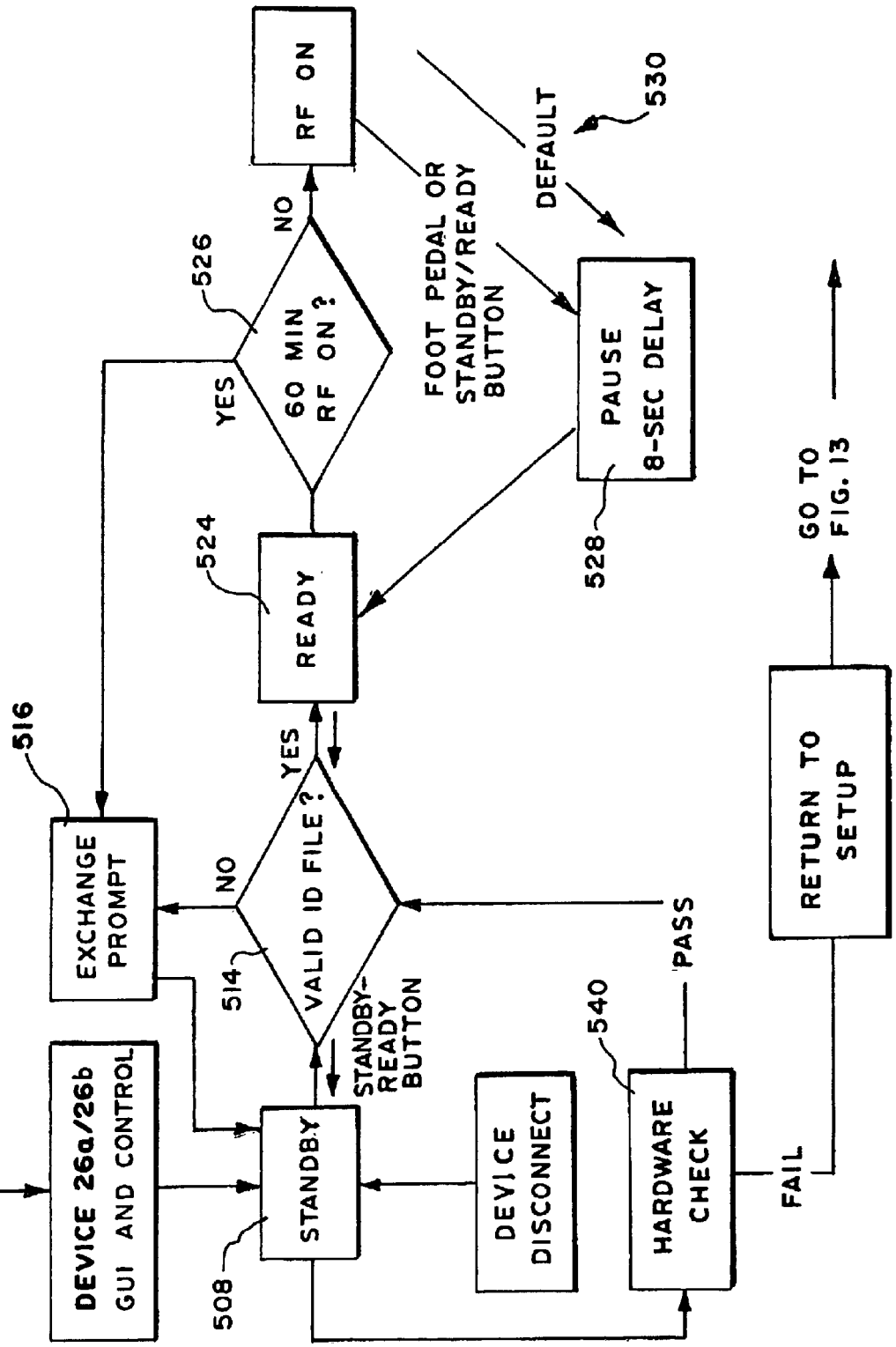
FIG. 15 is a flow chart showing further details of the pre-programmed rules implemented in concert with the pre-programmed rules shown in FIG. 13, by which information contained on the usage key card and provided by a selected treatment device is read and processed to enable use of the selected treatment device in association with the device shown in FIGS. 11A, 11B, and 12.

After the start-up logo and title image for the selected device 26a/26b has been displayed, the controller 52 remains in the STAND-BY mode 508 (see FIG. 15). In the STAND-BY mode 508, the controller 52 performs a DEVICE HARDWARE CHECK function 540. The same DEVICE HARDWARE CHECK function 540 is performed regardless of the device 26a/26b selected. The DEVICE HARDWARE CHECK function 540 looks for the presence or absence of a preestablished electrical identification signal from the device 26a/26b itself, to confirm by a different mechanism the identity of the device 26a/26b indicated by the user key card 202.

The DEVICE HARDWARE CHECK function 540 can be accomplished is various ways. For example, the device 26a and 26b can include within its handle an analog electrical element (e.g., a capacitor or resistor) or a solid state element (micro-chip, ROM, EEROM, EPROM, or non volatile RAM) that generates an electrical value that differs depending upon the device 26a or 26b is present. The controller 52 reads this electrical value through the electrical connector 408, to which the selected treatment device 26a/26b is coupled for use. The DEVICE HARDWARE CHECK function 540 provides a redundant, fail safe confirmation of the identification of the device 26a/26b provided by the user key card 202. If the identity of the device 26a/26b based upon the DEVICE HARDWARE CHECK function 540 does not correspond with the identity of the device 26a/26b based upon the user key card 202, the controller 52 returns to the SETUP prompt 500 (FIG. 14) described earlier, to repeat the identification process.

If the identification of the device 26a/26b based upon the user key card 202 and DEVICE HARDWARE CHECK function 540 correspond, the controller 52 executes the REGISTRATION function 514 for the device 26a/26b (see FIG. 15), to determine whether the user key card 202 inserted in the drive 426 contains a valid identification code 214. The same REGISTRATION function 514 is performed regardless of the device 26a/26b selected.

Figure 16:
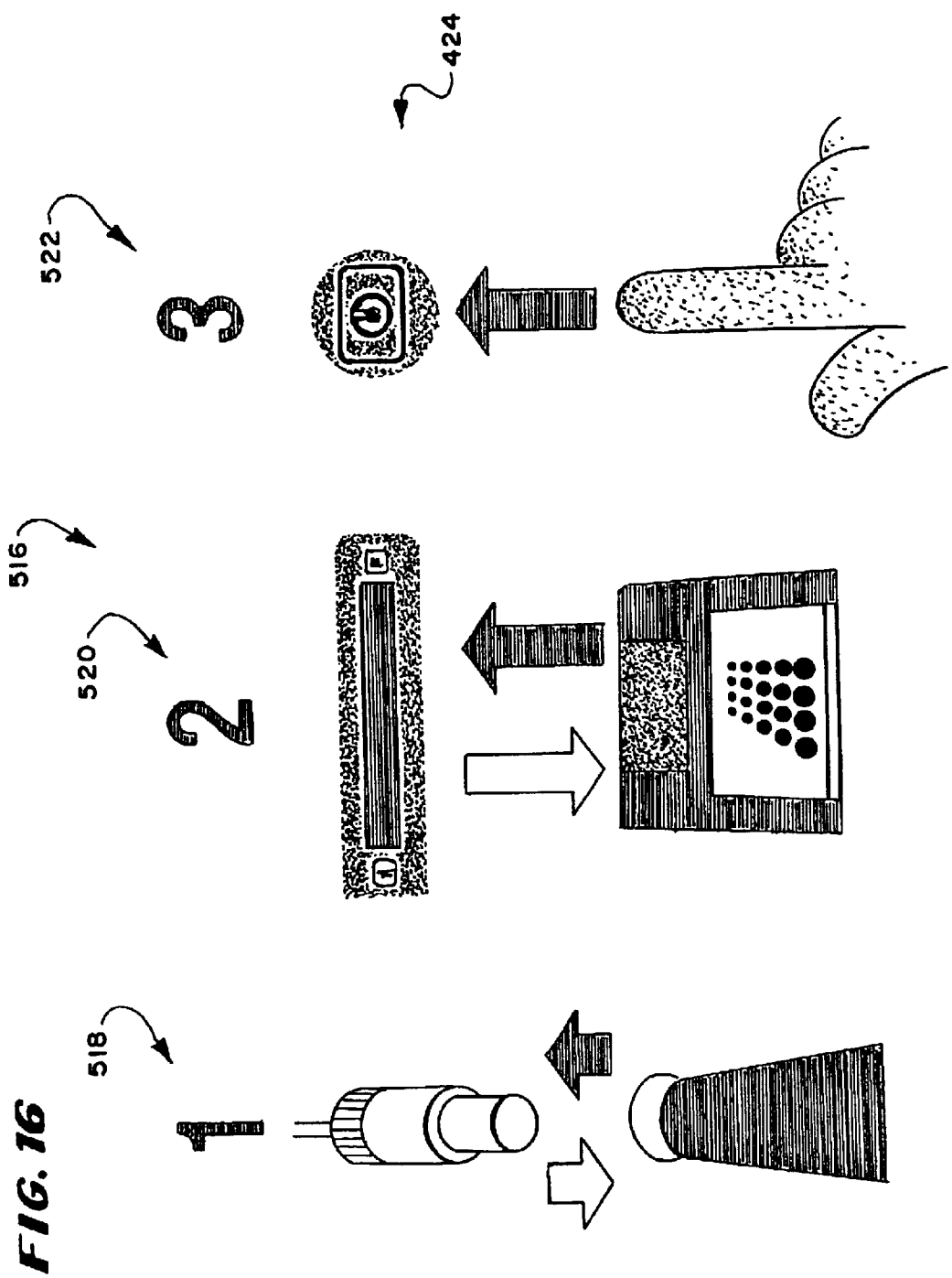
FIG. 16 is a representative EXCHANGE display that can be implemented by the graphical user interface of the device shown in FIGS. 11A, 11B, and 12, following the pre-programmed rules shown in FIGS. 13 and 15, as part of monitoring and controlling the use of a selected treatment device.

The identification code 214 will not be deemed valid when the code already exists in the use table 216 of the controller 52 with a time record 218 equal to or greater than the prescribed maximum, thereby indicating a completed prior use of the selected device 26a/26b. When the identification code 214 is not valid, the REGISTRATION function 514 commands the display microprocessor 474 to generate an EXCHANGE prompt 516 on the graphics display monitor 420. FIG. 16 shows a representative EXCHANGE prompt 516. When graphically implemented, as shown in FIG. 16, the EXCHANGE prompt 516 leads the operator in a step-wise fashion through the tasks of replacing the previously used selected device 26a/26b and its key card 202 with a new selected device 26a/26b and its associated key card 202.

As shown in FIG. 16, a first graphic field displays one or more icons and/or alpha-numeric indicia 518 that prompt the operator to disconnect the electrical connector 42 of the previously used treatment device 26a/26b and to connect a new treatment device 26a/26b. A second graphic field displays one or more icons and/or alpha-numeric indicia 520 that prompt the operator to remove the old user key card 202 and insert the new key card 202 that accompanied the new selected treatment device 26a/26b in the kit 200. A third graphic field displays one or more icons and/or alpha-numeric indicia 522 that prompt the user to again select the standby-ready button 430 on the housing 400.

With the new treatment device 26 connected and the new user key card 202 inserted in the floppy disk drive 426, selection of the standby-ready button 430 causes the controller 52 to again enter the STAND-BY mode 508, and again execute the DEVICE HARDWARE CHECK function 540 and the REGISTRATION function 514 (see FIG. 15).

Successful completion of the DEVICE HARDWARE CHECK function 540 and the REGISTRATION function 514, confirming the type of device 26a/26b and indicating the presence of a valid identification code 214 on the user card 202, causes the controller 52 to enter the READY mode 524.

B. Controlling Deployment and Use of the Selected Device

Upon completion of the START-UP operation, and successful registration of the usage key card 202, the controller 52 proceeds to condition the generator and ancillary equipment to proceed step-wise through a sequence of operational modes. The operational modes have been preprogrammed to achieve the treatment protocol and objective of the selected device 26a/26b. The conduct of these operational modes and the appearance of the graphical user interface that guides and informs the user during the course of the selected procedure can differ between devices 26a and 26b.

For ease of description, the GUI displays for the upper gastro-intestinal procedure (i.e., for the device 26a) will in shorthand be generally called UGUI (which are shown in FIGS. 12 and 17 to 24). Likewise, the GUI displays for the lower gastro-intestinal procedure (i.e., for the device 26b) will in shorthand be generally called LGUI (which are shown in FIGS. 25 to 30).

1. Standby

Figure 17:
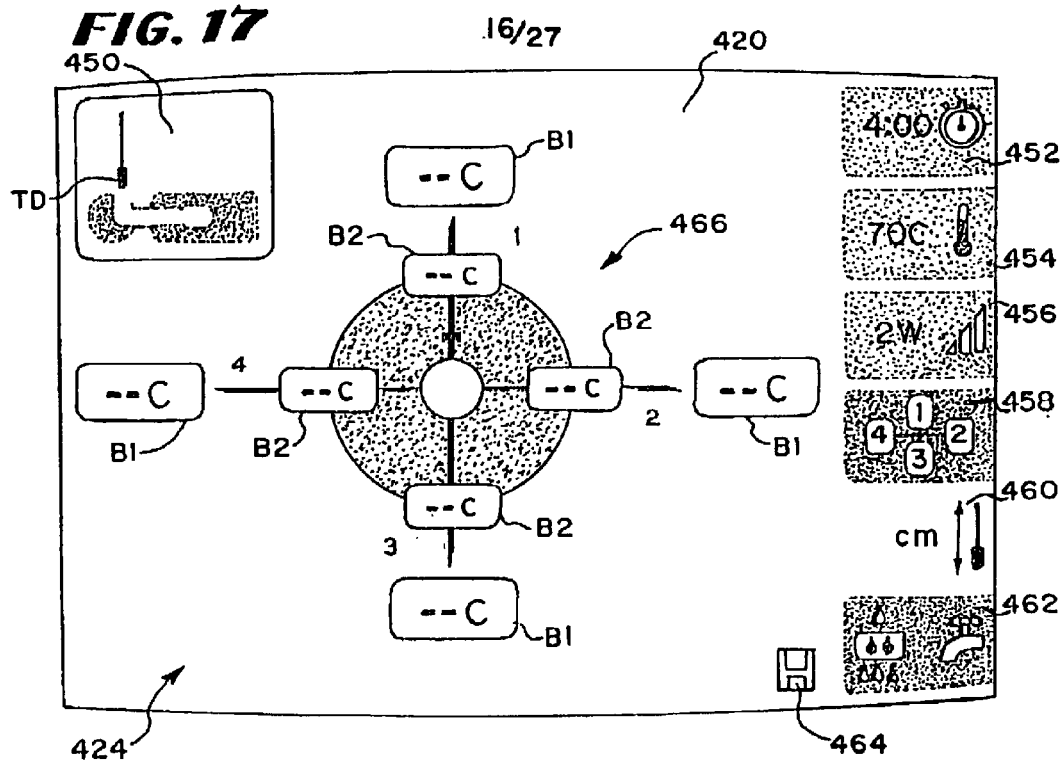
FIGS. 17 to 24 are views of a graphical user interface that can be implement by the device shown in FIGS. 11A, 11B, and 12, for controlling the use and operation of the treatment device shown in FIGS. 2 to 4.

When the device identification code 228a is read on the usage key card 202 (i.e., indicating selection of the device 26a for use in the upper gastro-intestinal tract), the controller 52 conditions the UGUI to display the Standby screen shown in FIG. 17. When the device identification code 228b is read on the usage key card 202 (i.e., indicating selection of the device 26b for use in the lower gastro-intestinal tract), the controller 52 conditions the LGUI to display the Standby screen shown in FIG. 25.

No radio frequency energy can be delivered while the Standby screen is displayed.

There are various icons common to the Standby, Ready, RF-On, and Pause screens for both UGUI and LGUI.

In the Standby screen for UGUI, a Screen Icon 450 appears in the upper left hand corner to indicate the operating condition of the treatment device 26a. In the UGUI, the icon 450 also indicates the position of the treatment device inside or outside the esophagus. In the Standby screen for the LGUI (see FIG. 25), the Screen Icon 450 is displayed in the lower left hand corner, to indicate the operating condition of the treatment device 26b.

While in the Standby Mode, the physician can couple the source of cooling liquid to the appropriate port on the handle of the device 26a/26b (as previously described) and load the tubing leading from the source of cooling liquid (e.g., a bag containing sterile water) in the pump rotor 428. The physician can also couple the aspiration source 46 to the appropriate port on the handle of the treatment device 26a/26b (as also already described). The physician can also couple the patch electrode 412 and foot pedal 416.

In UGUI (FIG. 17), there are also parameter icons designating target duration 452, target temperature 454, maximum power 456, channel selection 458, coagulation level 460, and flow rate/priming 462. These icons are aligned with, respectively, the corresponding Target Duration Keys 438, Target Temperature Keys 440, Maximum Power Keys 442, Channel Selection Keys 444, Coagulation Level Keys 446, and Flow Rate and Priming Keys 448. The icons 452 to 462 indicate current selected parameter values. The flow rate/priming icon 462 shows the selected pump speed by highlighting a single droplet image (low speed), a double droplet image (medium speed), and a triple droplet image (high speed).

In LGUI (FIG. 25), comparable parameter icons appear, except that coagulation level icon 460 in the UGUI is replaced in the LGUI by a RF cycle counter icon 461. The icon 461 displays a value that counts the number of RF cycles applied to the device 26b during use. Knowing the number of electrodes that the device 26b carries, this value is indicative of the number of lesions that are being formed.

Pressing the "Up" priming key 448 in the Standby mode, to cause cooling liquid to flow through the treatment device 26a, causes an animated priming stream PS to be displayed in the icon 450 (shown in FIG. 21) of the UGUI. An animated priming stream PS (see FIG. 26) is displayed in the flow rate/priming icon 462 of the LGUI when the device 26b is primed in the Standby mode. In other modes, animated priming streams PS are displayed in the Screen Icon 450 in UGUI (see FIGS. 21, 22, and 23) and LGUI (see FIGS. 28 and 29) whenever the pump rotor 428 is operating, to indicate the supply of cooling fluid through the respective treatment device 26a and 26b.

In both UGUI (FIG. 17) and LGUI (FIG. 25), there is also a floppy disk icon 464. The icon 464 is illuminated when a floppy disk is inserted in the drive 426. When the floppy disk (e.g., the usage key card 202) is inserted in the drive 426 data can be saved automatically after each application of radio frequency energy (as will be described later).

There is also an Electrode Icon 466 in each display UGUI and LGUI. The Electrode Icon 466 comprises an idealized graphical image, which spatially models the particular multiple electrode geometry of the treatment device 26a/26b selected to be deployed. The form of the Electrode Icon 466 is another way the controller 52 differentiates the UGUI and LGUI.

As FIG. 17 shows, in the UGUI, four electrodes are shown in the graphic image of the Icon 466, which are spaced apart by 90 degrees. This graphic image is patterned after the geometry of the four-electrode configuration of the device 26a, as shown in FIG. 4.

Figure 25:
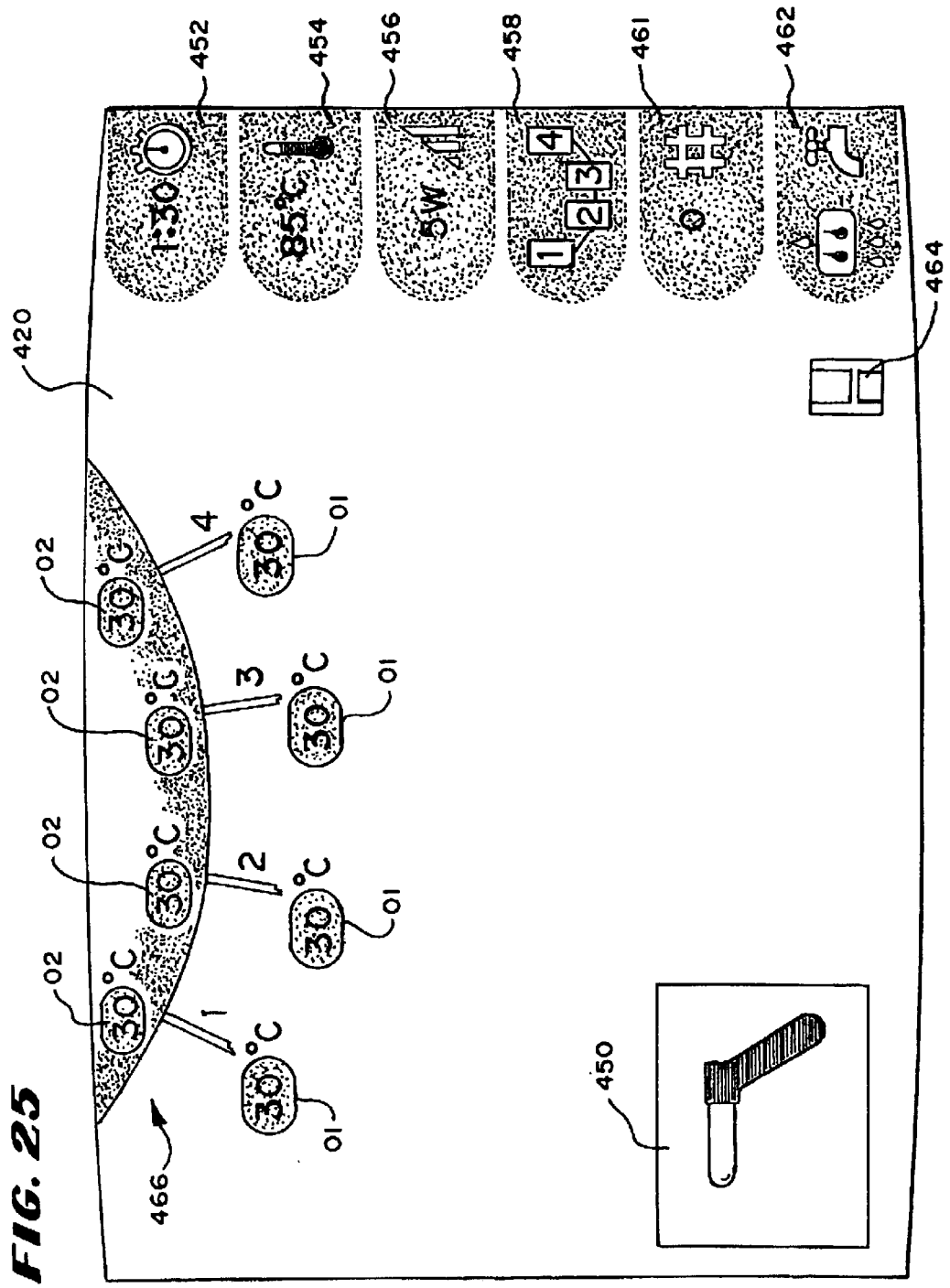
FIGS. 25 to 30 are views of a graphical user interface that can be implement by the device shown in FIGS. 11A, 11B, and 12, for controlling the use and operation of the treatment device shown in FIGS. 5 and 6.
Figure 26:
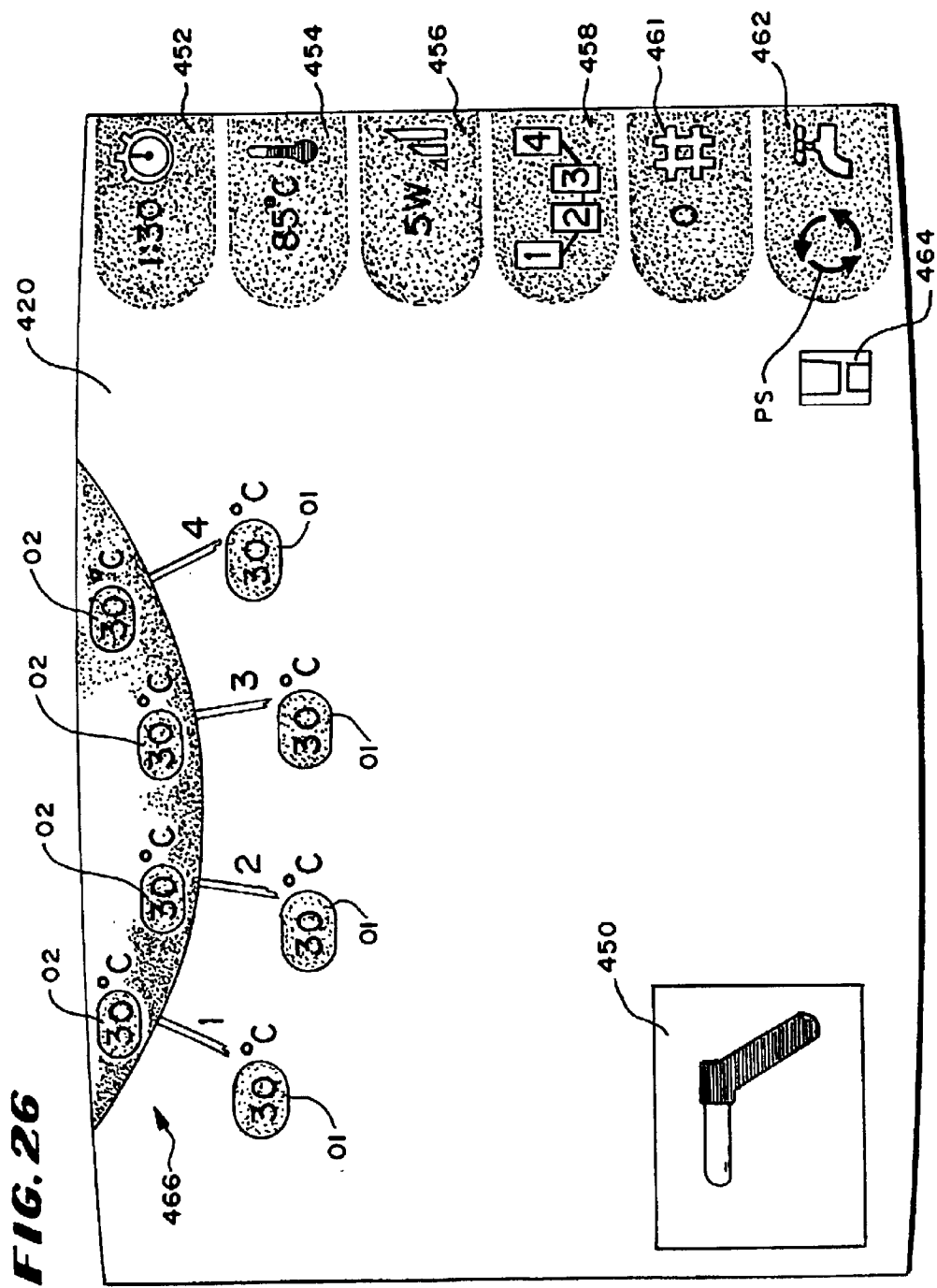

As FIG. 25 shows, in the LGUI, the four electrodes are shown in the graphic image of Icon 466 in a circumferentially spaced relationship along a partial arcuate sector. This graphic image is patterned after the arrangement of electrodes on the treatment device 26b, as shown in FIG. 6.

Figure 18:
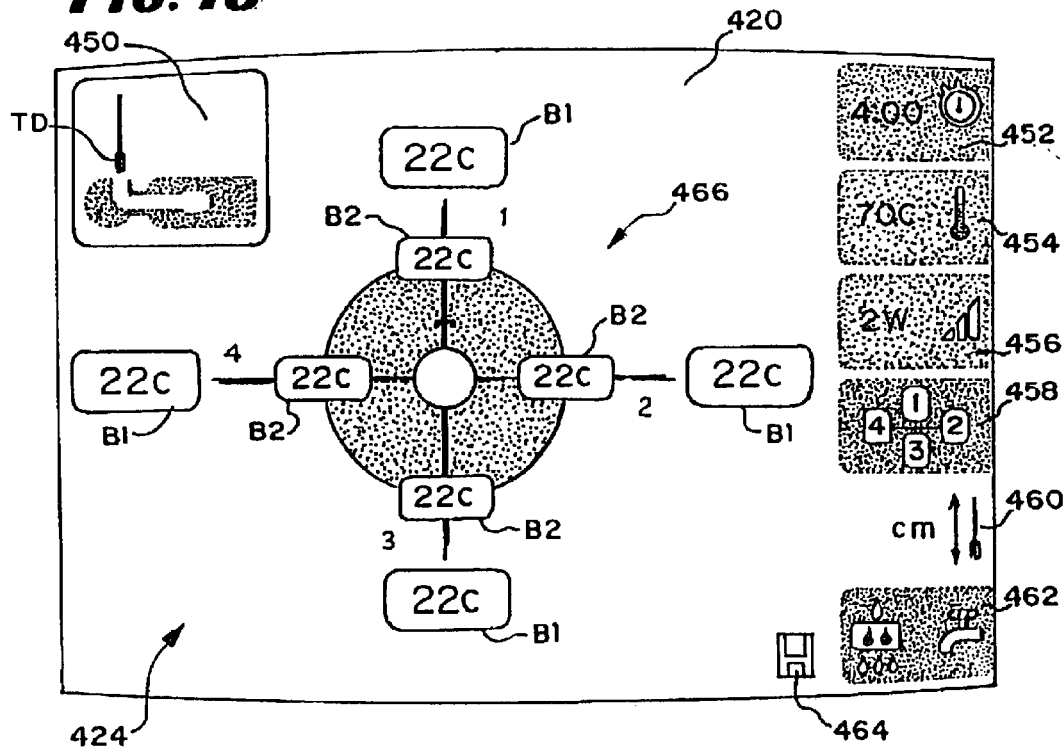

For each electrode, the Icon 466 presents in a spatial display the magnitude of tip temperature as actually sensed in outside box B1 in UGUI (FIG. 17) and in outside oval O1 in LGUI (FIG. 25). The magnitude of tissue temperatures as actually sensed are also displayed in inside box B2 in UGUI (FIG. 17) and in inside oval O2 in LGUI (FIG. 25) Until a functional treatment device 26a/26b is connected, two dashes will appear in the boxes B1/B2 (see FIG. 17) and the ovals O1/O2. The controller 52 prohibits advancement to the Ready screen until numeric values register in the boxes B1/B2 or ovals O1/O2, as FIG. 18 and FIG. 25 show, respectively. The display of numeric values indicate that a functional treatment device 26a/26b is present.

Figure 19:
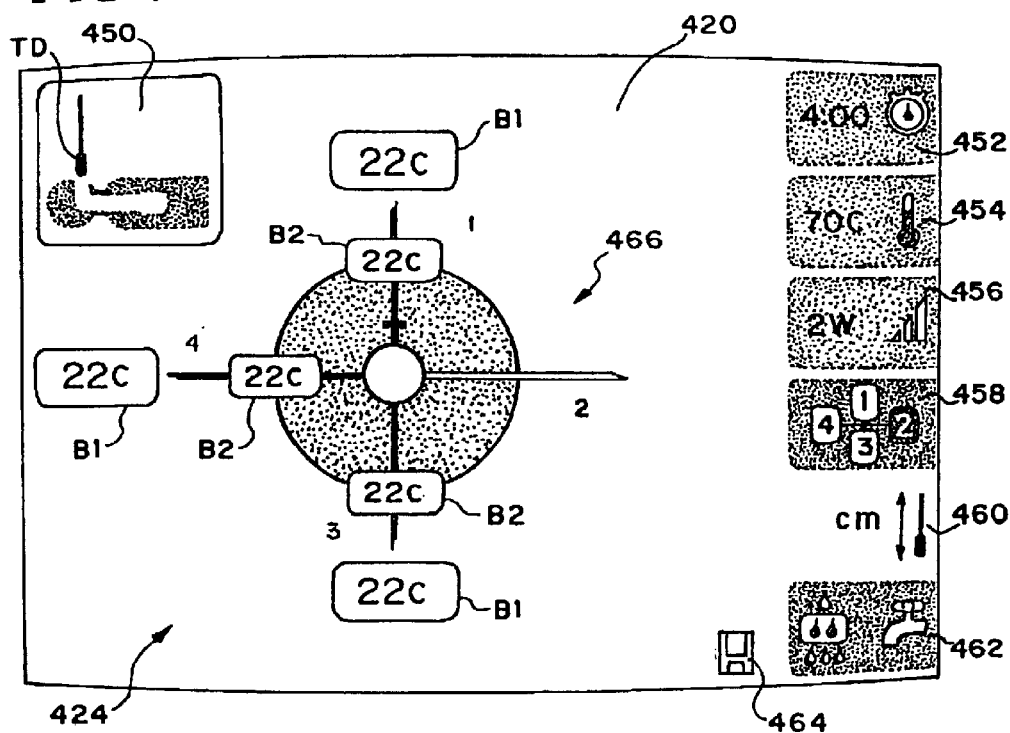

No boxes B1/B2 or ovals O1/O2 will appear in the Icon 466 for a given electrode if the corresponding electrode/channel has been disabled using the Channel Selection Keys 444, as FIG. 19 shows. In the illustrated embodiment, the physician is able to manually select or deselect individual electrodes using the Selection Keys 444 in the Standby or Ready Modes, but not in the RF-On Mode. However, the controller 52 can be configured to allow electrode selection while in the RF-On Mode, if desired.

The physician can now deploy the treatment device 26a/26b to the targeted tissue region. Once deployed, the physician extends the electrodes through mucosal tissue and into underlying smooth muscle, as FIG. 32 shows for the device 26a and FIG. 33 shows for the device 26b.

Once the treatment device 26a/26b is located at the desired location and the electrodes are deployed, the physician presses the Standby/Ready Button 430 to advance the controller 52 from Standby to Ready Mode.

2. Ready

In the Ready Mode, the controller 52 commands the generator 38 to apply bursts of low level radio frequency energy through each electrode selected for operation. Based upon the transmission of these low level bursts of energy by each electrode, the controller 52 derives a local impedance value for each electrode. The impedance value indicates whether or not the given electrode is in desired contact with submucosal, smooth muscle tissue.

Figure 20:
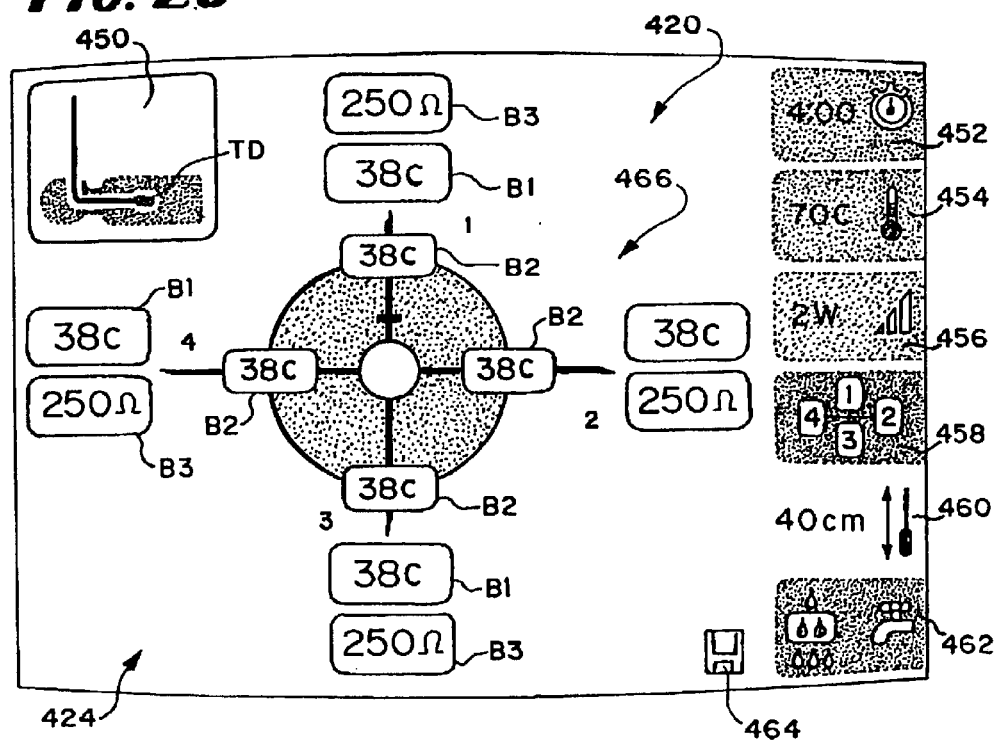
Figure 21:
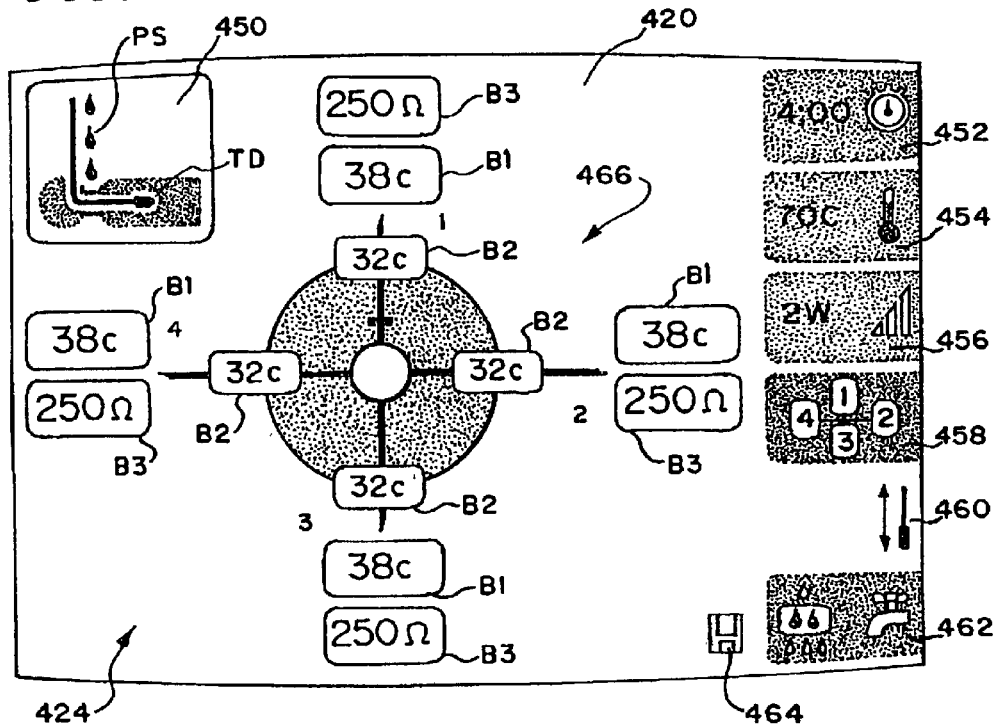
Figure 22:
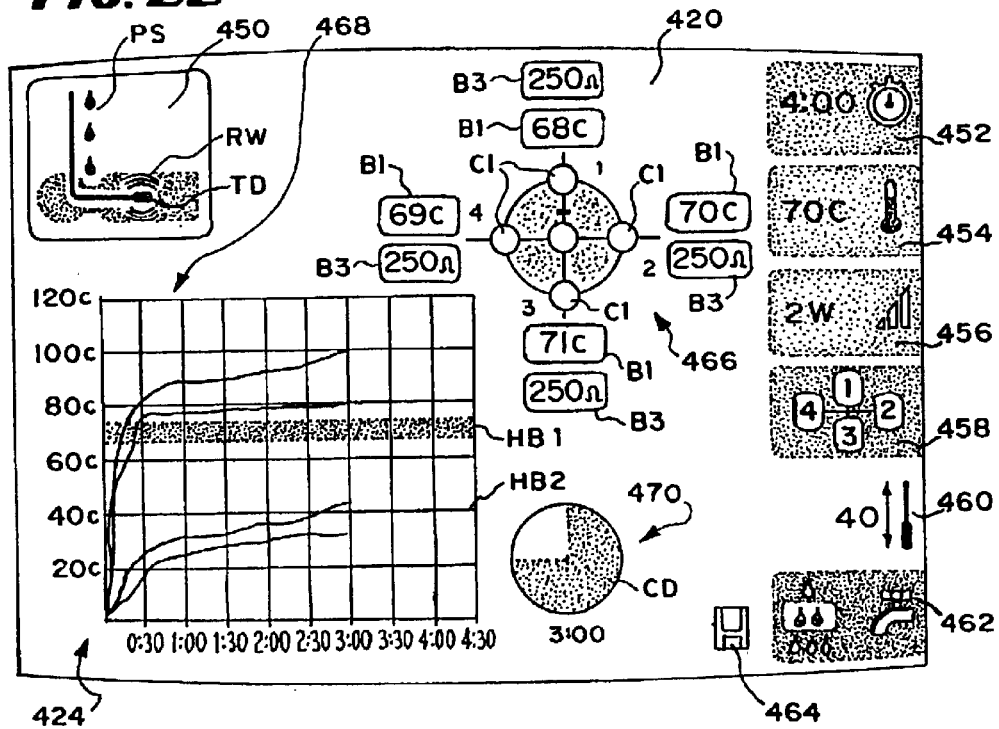
Figure 23:
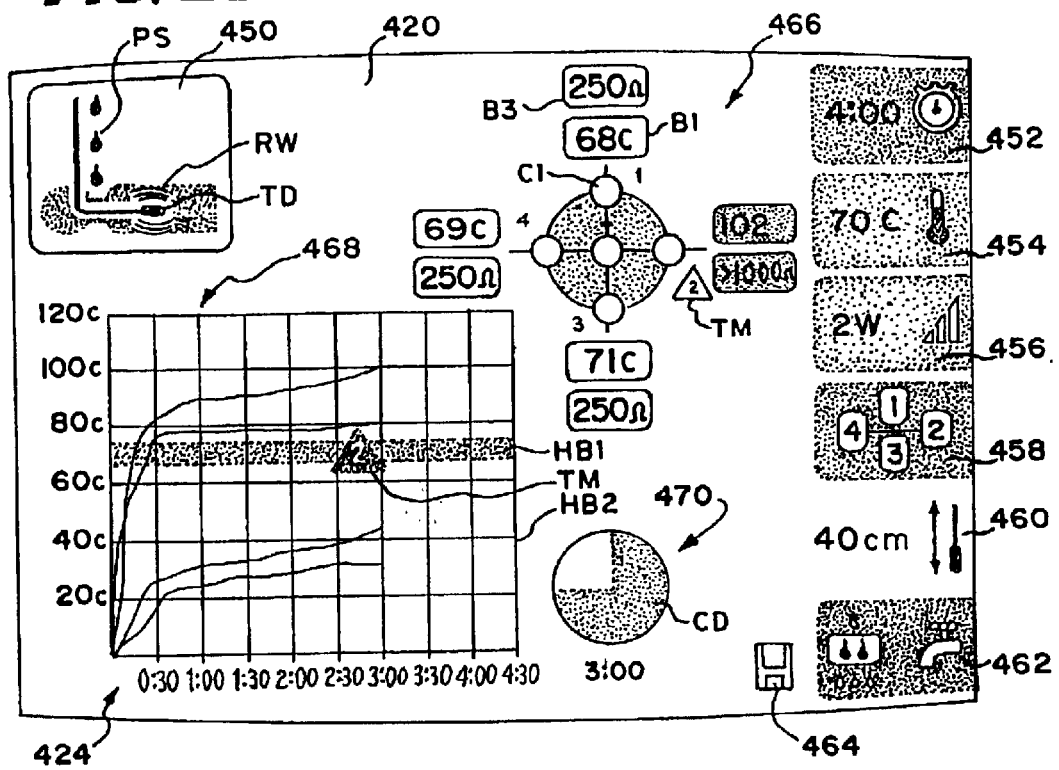
Figure 24:
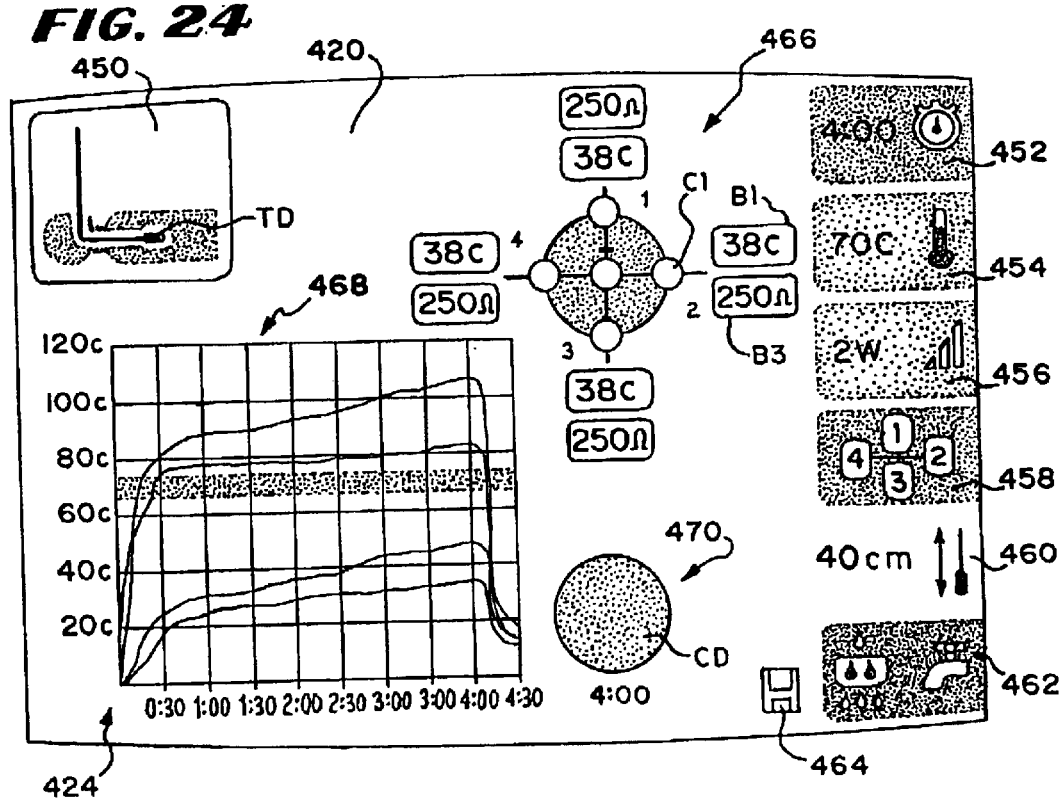

As FIG. 20 shows, the Ready screen updates the Screen Icon 450 of the UGUI to indicate that the treatment device 26a is connected and deployed in the patient's esophagus. The Ready screen of the UGUI also intermittently blinks the RF On Indicator 434 (see FIG. 12) to indicate that bursts of radio frequency energy are being applied by the electrodes. The Ready screen also updates the Electrode Icon 466 to spatially display in the inside and outside boxes B1 and B2 the actual sensed temperature conditions. The Ready screen also adds a further outside box B3 to spatially display the derived impedance value for each electrode.

In the LGUI (see FIG. 27), the Ready screen intermittently blinks a portion of the image in the icon 450 to indicate that bursts of radio frequency energy are being applied by the electrodes. The Ready screen also updates the Electrode Icon 466 to spatially display in the inside and outside ovals O1 and O2 the actual sensed temperature conditions. The Ready screen also adds a further outside oval O3 to spatially display the derived impedance value for each electrode.

On the Ready screen for both UGUI and LGUI, instantaneous, sensed temperature readings from the tip electrode and tissue surface, as well as impedance values, are continuously displayed in spatial relation to the electrodes (in the boxes B1, B2, and B3 in UGUI (FIG. 20) and in the ovals O1, O2, and O3 in LGUI (FIG. 27)). An "acceptable" color indicator (e.g., green) is also displayed in the background of box B1/oval O1 as long as the tip temperature reading is within the desired pre-established temperature range (e.g., 15 to 120 C). However, if the tip temperature reading is outside the desired range, the color indicator changes to an "undesirable" color indicator (e.g., to white), and two dashes appear in box B1/oval O1 instead of numeric values.

The controller 52 prevents the application of radio frequency energy if any temperature reading is outside a selected range (e.g., 15 to 120 degrees C.).

By touching the Target Duration Keys 438, the Target Temperature Keys 440, the Maximum Power Keys 442, the Channel Selection Keys 444, the Coagulation Level Keys 446, and the Flow Rate and Priming Keys 448 (see FIG. 12), the physician can affect changes to the parameter values for the intended procedure. The controller 52 automatically adjusts to take these values into account in its control algorithms. The corresponding target duration icon 452, target temperature icon 454, maximum power icon 456, channel selection icon 458, coagulation level icon 460, and flow rate/priming icon 462 change accordingly in the UGUI and LGUI to indicate the current selected parameter values.

When the physician is ready to apply energy to the targeted tissue region to begin treatment, the physician presses the foot pedal 416. In response, the controller 52 advances from Ready to RF-On Mode, provided that all sensed temperatures are within the selected range.

3. RF-On

When the foot pedal 416 is pressed, the controller 52 activates the pump rotor 428. Cooling liquid is conveyed through the treatment device 26a/26b into contact with mucosal tissue at the targeted site. At the same time, cooling liquid is aspirated from the treatment device 26a/26b in an open loop. During a predetermined, preliminary time period (e.g. 2 to 5 seconds) while the flow of cooling liquid is established at the site, the controller 52 prevents the application of radio frequency energy.

Figure 28:
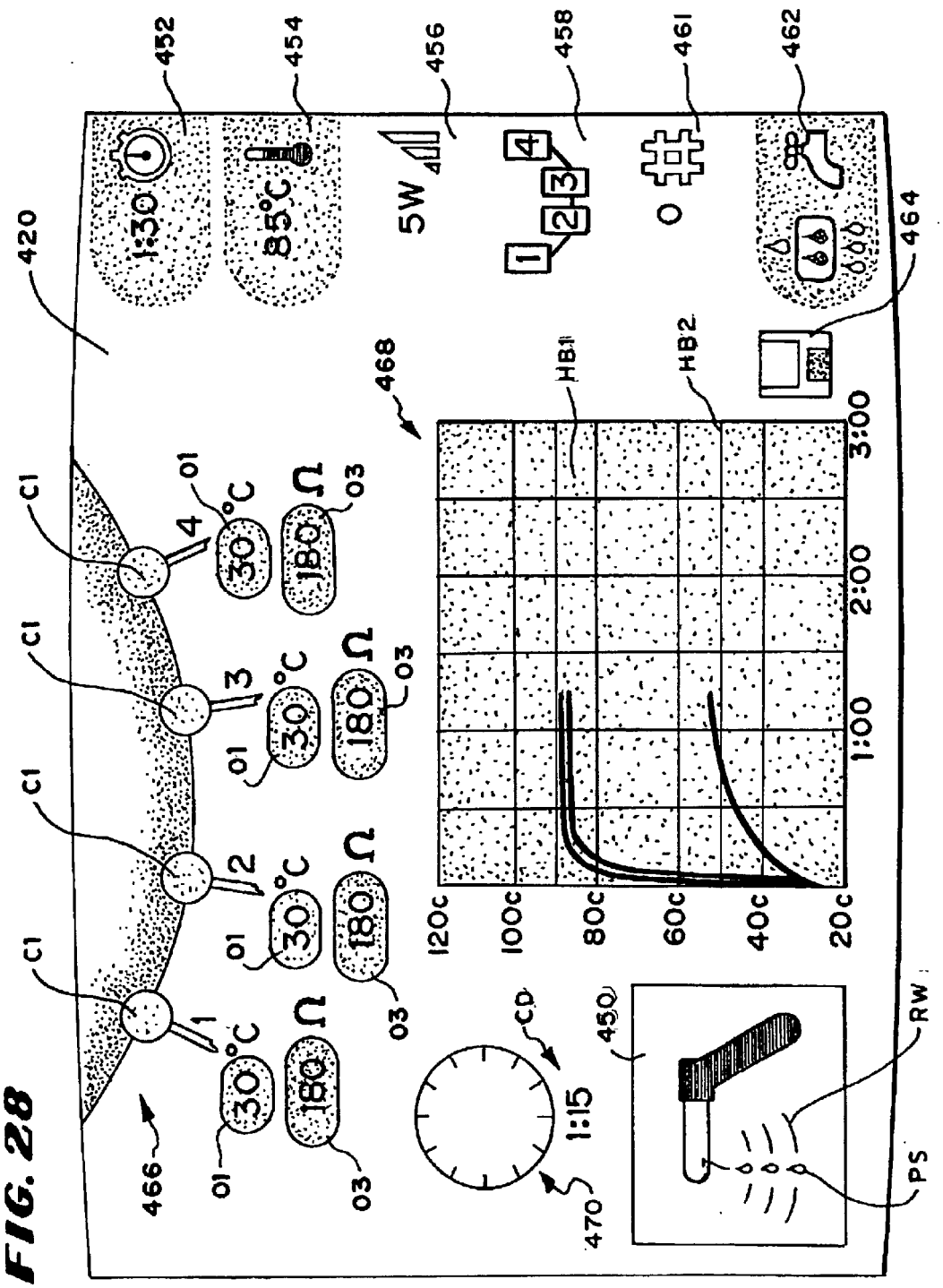
Figure 29:
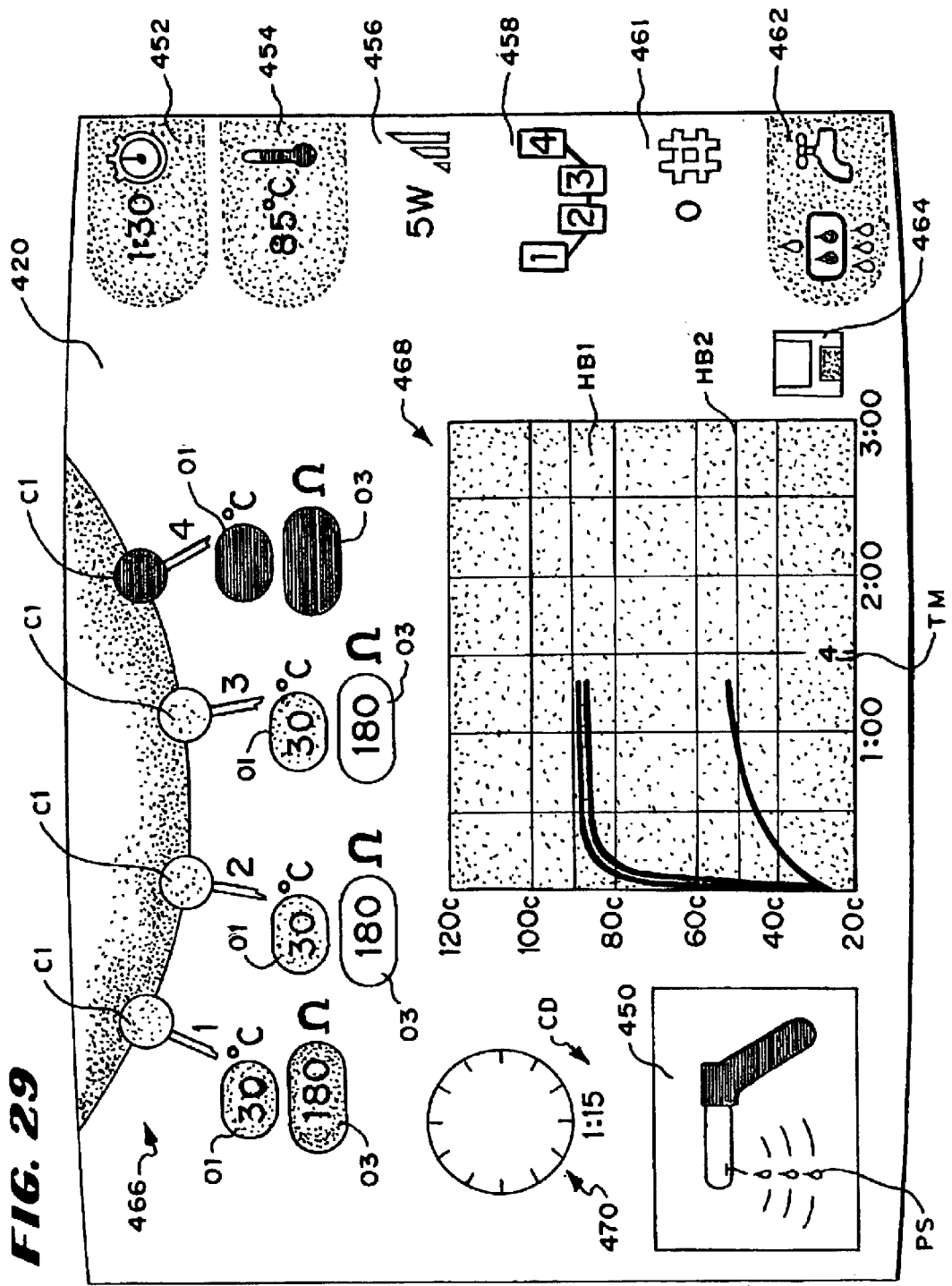
Figure 30:
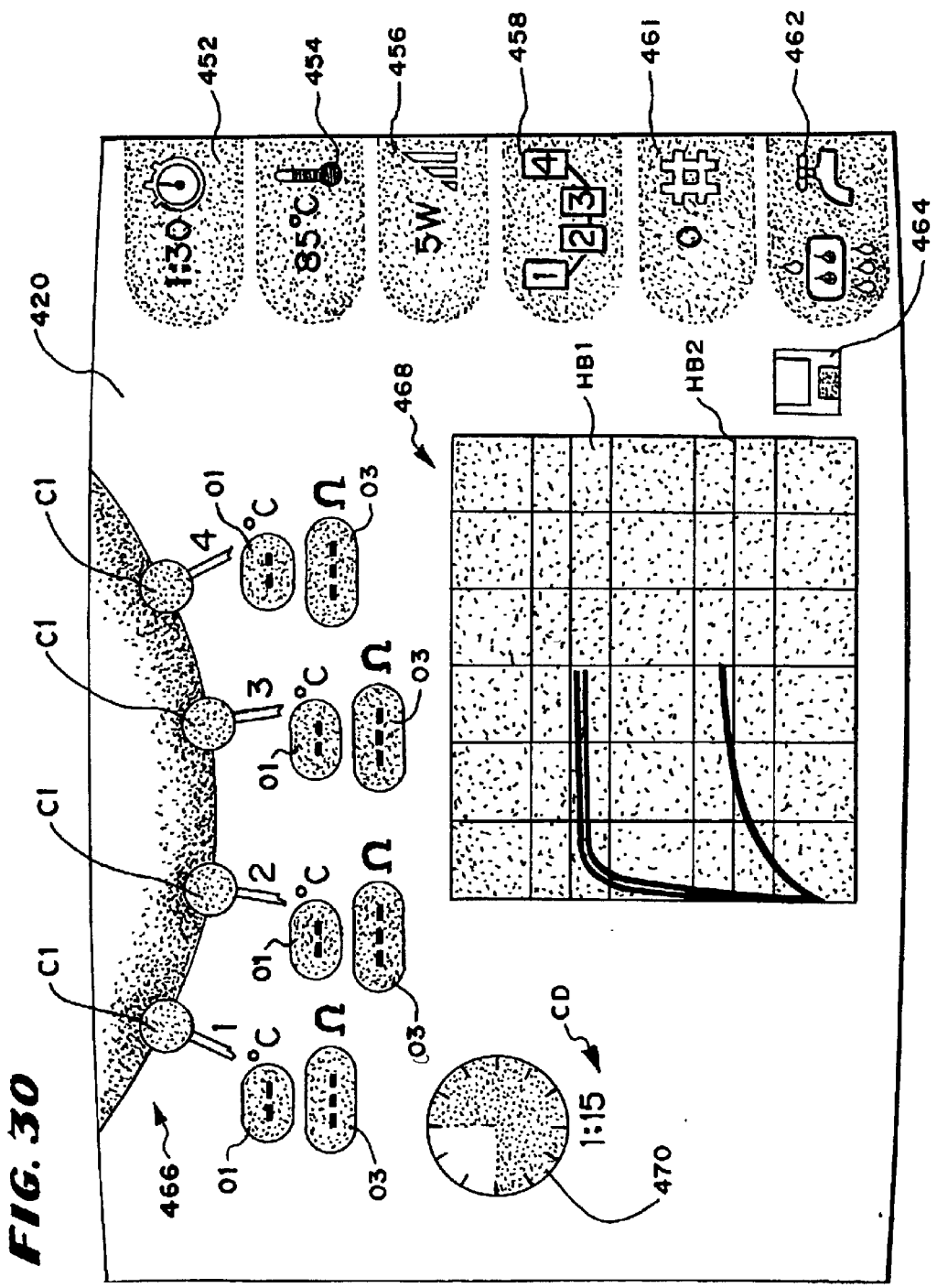

After the preliminary time period, the controller 52 applies radio frequency energy through the electrodes. The RF-On screen is displayed in the UGUI (FIG. 22) and LGUI (FIG. 28).

Figure 27:
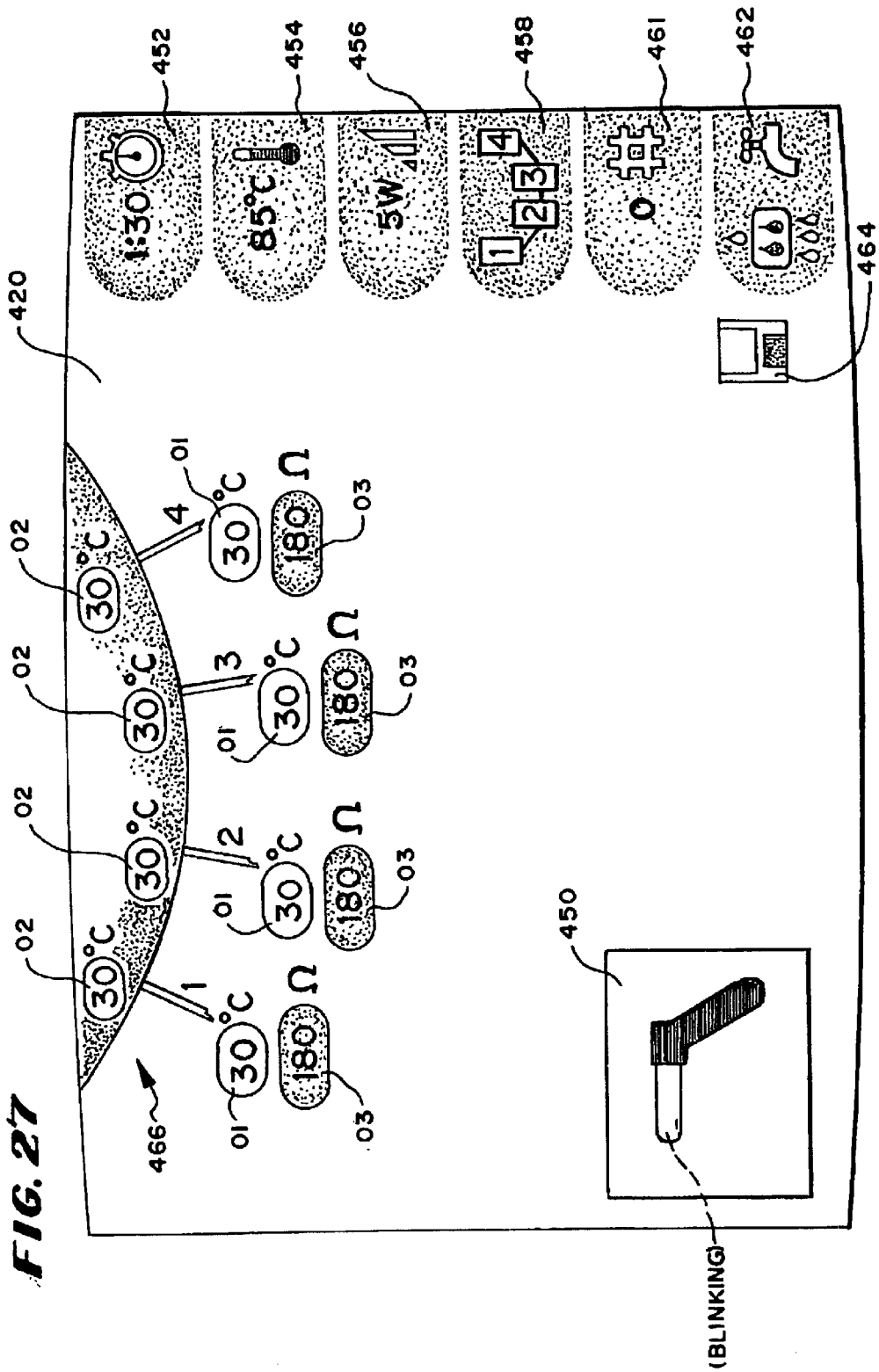

The RF-On screen in both the UGUI (FIG. 22) and LGUI (FIG. 28) displays the Screen Icon 450, indicate that the treatment device 26a/26b is connected and deployed. In the LGUI (FIG. 28), the Screen Icon 450 also shows the extension of electrodes, to differentiate the RF-On Screen from the Ready Screen (FIG. 27). The flow drop animation PS also appears in both UGUI (FIG. 22) and LGUI (FIG. 28), indicating that cooling is taking place. A flashing radio wave animation RW also appears in both UGUI (FIG. 22) and LGUI (FIG. 28), indicating that radio frequency energy is being applied. The RF On Indicator 434 (FIG. 12) is also continuously illuminated to indicate that radio frequency energy is being applied by the electrodes. FIG. 12 shows the RF-On screen of the UGUI.

In both UGUI (FIG. 22) and LGUI (FIG. 28), the RF-On screen also updates the Electrode Icon 466 to display in the boxes B1/ovals O1 the actual sensed tip temperature conditions. In both UGUI and LGUI, the RF-On screen also displays the derived impedance value for each electrode in the boxes B3/ovals O3.

In both UGUI (FIG. 22) and LGUI (FIG. 28), unlike the Ready or Standby screens, the surface temperature is no longer displayed in a numerical format in boxes B2/ovals O2. Instead, a circle C1 is displayed in both UGUI and LGUI, which is color coded to indicate whether the surface temperature is less than the prescribed maximum (e.g., 45 degrees C.). If the surface temperature is below the prescribed maximum, the circle C1 is colored an "acceptable" color, e.g., green. If the surface temperature is exceeds the prescribed maximum, the color of the circle C1 changes to an "not acceptable" color, e.g., to red.

Likewise, in addition to displaying numeric values in UGUI (FIG. 22) and LGUI (FIG. 28), the boxes B1 and B3/ovals O1 and O3 are also color coded to indicate compliance with prescribed limits. If the tip temperature is below the prescribed maximum (e.g., 100 degrees C.), the box B1/oval O1 is colored, e.g., green. If the tip temperature is exceeds the prescribed maximum, the box border thickens and the color of the box B1/oval O1 changes, e.g., to red. If the impedance is within prescribed bounds (e.g., between 25 ohms and 1000 ohms), the box B3/oval O3 is colored, e.g., grey. If the impedance is outside the prescribed bounds, the box border thickens and the color of the box B3/oval O3 changes, e.g., to red.

If desired, in either or both UGUI and LGUI, the Electrode Icon 466 can also display in a box or circle the power being applied to each electrode in spatial relation to the idealized image.

In both UGUI (FIG. 22) and LGUI (FIG. 28), the RF-On screen displays the target duration icon 452, target temperature icon 454, maximum power icon 456, channel selection icon 458, coagulation level icon 460 (or, in LGUI, the RF cycle icon 461), and flow rate/priming icon 462, indicating the current selected parameter values. The physician can alter the target duration or target temperature or maximum power and pump flow rate through the corresponding selection keys 438, 440, 442, and 448 (see FIG. 12) on the fly, and the controller 52 and respective UGUI and LGUI instantaneously adjust to the new parameter settings. As before mentioned, in the illustrated embodiment, the controller 52 does not permit change of the channel/electrode while radio frequency energy is being applied, and, for this reason, the channel selection icon 458 is dimmed.

Unlike the Standby and Ready screens, the RF-On screen in both UGUI (FIG. 22) and LGUI (FIG. 28) also displays a real time line graph 468 to show changes to the temperature profile (Y-axis) over time (X-axis). In both UGUI (FIG. 22) and LGUI (FIG. 28), the RF-On screen also shows a running clock icon 470, which changes appearance to count toward the target duration. In the illustrated embodiment, a digital clock display CD is also shown, indicating elapsed time.

The line graph 468 in both UGUI (FIG. 22) and LGUI (FIG. 28) displays four trending lines to show the minimum and maximum surface and tip temperature readings from all active electrodes. In the illustrated embodiment, the time axis (X-axis) is scaled to one of five pre-set maximum durations, depending upon the set target duration. For example, if the target duration is 0 to 3 minutes, the maximum time scale is 3:30 minutes. If the target duration is 3 to 6 minutes, the maximum time scale is 6:30 seconds, and so on.

The line graph 468 displays two background horizontal bars HB1 and HB2 of different colors. The upper bar HB1 is colored, e.g., green, and is centered to the target coagulation temperature with a spread of plus and minus 10 degrees C. The lower bar HB2 is colored, e.g., red, and is fixed at a prescribed maximum (e.g., 40 degrees C.) to alert potential surface overheating.

In both UGUI (see FIG. 23) and LGUI (see FIG. 29), the line graph 468 also displays a triangle marker TM of a selected color (e.g., red) and with a number corresponding to the channel/electrode that is automatically turned off by the controller 52 due to operation outside the selected parameters. As before described, the circle C1 and boxes B1 and B3/ovals O1 and O3 for this electrode/channel are also modified in the electrode icon 466 when this situation occurs.

The Electrode Icon 466 can graphically display other types of status or configuration information pertinent to the treatment device 26a/26b. For example, the Electrode Icon 466 can display a flashing animation in spatial relation to the idealized electrodes to constantly remind the physician that the electrode is extended into tissue. The flashing animation ceases to be shown when the electrode is retracted. The flashing animation reminds the physician to retract the electrodes before removing the treatment device 26a/26b. As another example, the Electrode Icon 466 can display another flashing animation when the expandable structure of the treatment device 26a is expanded. The flashing animation reminds the physician to collapse the electrodes before removing the treatment device 26a.

4. Pause

For the UGUI (FIG. 24) and the LGUI (FIG. 30), the controller 52 terminates the conveyance of radio frequency ablation energy to the electrodes and the RF-On screen changes into the Pause screen, due to any of the following conditions (i) target duration is reached, (ii) all channels/electrodes have an erroneous coagulation condition (electrode or surface temperature or impedance out of range), or (iii) manual termination of radio frequency energy application by pressing the foot pedal 416 or the Standby/Ready Button 430.

Upon termination of radio frequency ablation energy, the running clock icon 470 of the Pause screen of the UGUI (FIG. 24) and the LGUI (FIG. 30) stops to indicate total elapsed time. The controller 52 commands the continued supply of cooling liquid through the treatment device 26a/26b into contact with mucosal tissue at the targeted site. At the same time, cooling liquid is aspirated from the treatment device 26a/26b in an open loop. This flow of cooling liquid continues for a predetermined time period (e.g. 2 to 5 seconds) after the supply of radio frequency ablation energy is terminated, after which the controller 52 stops the pump rotor 428.

The Pause screen for the UGUI (FIG. 24) and LGUI (FIG. 30) is in most respects similar to the RF-On screen for the respective device 26a/26b. In the UGUI (FIG. 24), the Pause screen displays the Screen Icon 450, to indicate that the treatment device 26a is connected and deployed in the patient's esophagus. However, the flashing radio wave animation is not present, indicating that radio frequency energy is no longer being applied. In the LGUI (FIG. 30), the Screen Icon 450 is blanked.

The Pause screen for the UGUI (FIG. 24) also updates the Electrode Icon 466 to display in the boxes B1 and B3 the actual sensed tip temperature and impedance conditions. However, no background color changes are registered on the Pause screen, regardless of whether the sensed conditions are without or outside the prescribed ranges. In the LGUI (FIG. 30), no values are displayed in the ovals O1 and O3.

The Pause screen for the UGUI (FIG. 24) and the LGUI (FIG. 30) continues to display the target duration icon 452, target temperature icon 454, maximum power icon 456, channel selection icon 458, coagulation level icon 460 (or, in LGUI, the RF cycle icon 461), and flow rate/priming icon 462, indicating the current selected parameter values.

In the UGUI (FIG. 24) and LGUI (FIG. 30), the real time temperature line graph 468 continues to display the four trending lines, until the target duration is reached and five additional seconds elapse, to show the drop off of electrode temperature.

If further treatment is desired, pressing the Standby/Ready button 430 returns the device 400 from the Pause back to the Ready mode.

V. The Procedure Log

When the floppy disk (i.e., usage key card) is inserted in the drive 426, data is saved automatically after each application of radio frequency energy.

When the floppy disk is inserted, the controller 52 downloads data to the disk each time it leaves the RF-On screen, either by default or manual termination of the procedure. The downloaded data creates a procedure log. The log documents, by date of treatment and number of treatments, the coagulation level, the coagulation duration, energy delivered by each electrode, and the coolant flow rate. The procedure log also records at pre-established intervals (e.g., every 5 seconds) the temperatures of the electrode tips and surrounding tissue, impedance, and power delivered by each electrode. The procedure log preferably records these values in a spreadsheet format.

The controller 52 includes an UPDATE function 526 (see FIG. 15). The UPDATE function 526 registers the time period during which radio frequency energy is applied using the device 26a/26b. The time is entered into the time record 218 of the use table 216 maintained by the controller 52. After a prescribed maximum period of use is registered (e.g., sixty minutes), the UPDATE function 526 interrupts application of radio frequency energy to the electrodes 66, and prevents further delivery by the generator 38 to the particular device 26.

In this circumstance, the UPDATE function 526 causes the controller 52 to generate the EXCHANGE prompt 516. As previously described, the EXCHANGE prompt 516 (see FIG. 16) requires the operator to replace the existing device 26 and its key card 200 with a new device 26 and its associated key card 200.

The housing 400 can carry an integrated printer, or can be coupled through the I/O device 54 to an external printer. The printer prints a procedure log in real time, as the procedure takes place.

Other details of the GUI during operation of a given device 26a/26b can be found in co-pending U.S. patent application Ser. No. 09/305,123, filed May 4, 1999 and entitled "Graphical User Interface for Association with an Electrode Structure Deployed in Contact with a Tissue Region," which is incorporated herein by reference.

Various features of the invention are set forth in the following claims.

We claim:

1. A system for controlling operation of a family of treatment devices comprising
    a family of treatment devices comprising at least first and second different treatment devices which are intended to be individually deployed for use in different tissue regions,
    a controller including a connector to which a selected one of the first or second treatment device is coupled for use,
    a reader to download information to the controller to identify the selected treatment device coupled to the connector, the information comprising first data containing an identification code unique to the selected treatment device and second data containing a functional code identifying a functional characteristic of the selected device, the identification codes and the functional codes for the first and second treatment devices being different, the controller including a usage monitoring function comprising a first data stare prior to downloading of the identification code and operating to process the identification code and enabling operation of the selected device if the identification code correlates in a pre-established manner with the first data state, the usage monitoring function further operating, in response to enabling operation of the selected device, to change the first data state to a second data state that prevents subsequent operation of the selected device in response to downloading of the identification code,
    the controller also including a first or second control function enabled only if the usage monitoring function enables operation of the selected device, the first control function being enabled in response to downloading the functional code of the first treatment device and the second control function being enabled in response to downloading of the functional code of the second treatment device, and
    the controller further including an operating system to execute on a display screen a first graphical interface guiding and monitoring use of the first treatment device when the first control function is enabled and a second graphical interface different, at least in part, from the first graphical interface and guiding and monitoring use of the second treatment device when the second control function is enabled.

2. A system according to claim 1 further including
    a first usage key card for the first treatment device and a second usage key card for the second treatment device, each usage key card adapted to be handled separate from the respective treatment device and comprising a storage medium formatted to contain, for the respective treatment device, the identification code and the functional code that, upon reading by the reader, is downloaded to the controller.

3. A system according to claim 1
    wherein the usage monitoring function causes the controller to create a table by registering unlike identification codes in memory as they are downloaded by the reader and to enable the control function for the selected treatment device when a new identification code is registered in the table.

4. A system according to claim 3
wherein the operating system displays a viewable image to prompt input to create the table for the selected treatment device using the usage monitoring function.

5. A system according to claim 3
wherein the usage monitoring function causes the controller to disable the first or second control function for the selected treatment device when the given identification code matches an identification code in the table.

6. A system according to claim 5
wherein the operating system displays a viewable image to prompt exchange of the selected treatment device when the control function for the selected treatment device is disabled as a result of the usage monitoring function.

7. A system according to claim 3
wherein the usage monitoring function causes the controller to register in the table, a time period of use of the device.

8. A system according to claim 7
wherein the usage monitoring function causes the controller to disable the control function for the selected treatment device when the time period of use exceeds a prescribed period.

9. A system according to claim 8
wherein the operating system displays a viewable image to prompt exchange of the selected treatment device when operation of the selected treatment device is disabled as a result of the usage monitoring function.

10. A system according to claim 1
wherein the reader downloads through the connector an electrical identification signal that varies according to the identification and functional codes of the selected treatment device.

11. A system according to claim 1
wherein first graphical interface includes an idealized image of the first treatment device, and
wherein second graphical interface includes an idealized image of the second treatment device.

12. A system according to claim 11
wherein the idealized image of the first treatment device differs from the idealized image of the second treatment device.

13. A system according to claim 1
wherein at least one of the first and second graphical interfaces includes an indicator image to represent a monitored operating condition affecting the selected treatment device.

14. A system according to claim 1
wherein the controller includes an input adapted to be attached to a sensor carried by the selected treatment device to monitor an operating condition, and
wherein the graphical interface for the selected treatment device includes an indicator image to represent the operating condition monitored by the sensor.

15. A system according to claim 14
wherein the sensor monitors tissue temperature.

16. A system according to claim 14
wherein the sensor monitors impedance.

17. A system according to claim 14
wherein the indicator image displays a value to represent the monitored operating condition.

18. A system according to claim 14
wherein the indicator image displays a color to represent the monitored operating condition.

19. A system according to claim 14
wherein the graphical interface for the selected treatment device includes a second indicator image to represent changes in the monitored operating condition over time.

20. A system according to claim 14
wherein the controller includes an output to process the monitored operating condition as data for storage or manipulation.

21. A system according to claim 20
wherein the output communicates with a storage medium to save the data.

22. A system according to claim 20
wherein the output communicates with a printer to print the data.

23. A system according to claim 1
wherein at least one of the first and second graphical interfaces includes an animated visual image.

24. A method for controlling operation of a family of treatment devices comprising the steps of
providing a family of treatment devices comprising at least first and second different treatment devices which, in use, are intended to be individually deployed in association with different tissue regions,
selecting one of the first or second treatment device for use,
connecting the selected treatment device to a unified controller having a first control function for the first treatment device and a second control function for the second treatment device,
communicating to the controller through a reader information relating to the selected treatment device coupled to the connector, the information comprising first data containing an identification code unique to the selected treatment device and second data containing a functional code identifying a functional characteristic of the selected device, the identification codes and the functional codes for the first and second treatment devices being different,
executing a usage monitoring function having a first data state prior to downloading of the identification code and operating to process the identification code and enabling operation of the selected device only if the identification code correlates in a pre-established wanner with the first data state, the usage monitoring function further operating, in response to enabling operation of the selected device, to change the first data state to a second data state that prevents subsequent operation of the selected device in response to downloading of the identification code,
enabling either the first or second control function only if the usage monitoring function enables operation of the selected device, the first control function being enabled in response to downloading the functional code of the first treatment device and the second control function being enabled in response to downloading of the functional code of the second treatment device,
enabling execution on a display screen of a first graphical interface guiding and monitoring use of the first treatment device when the first control function is enabled, and enabling execution on a display screen of a second graphical interface different, at least in part, from the first graphical interface and guiding and monitoring use of the second treatment device when the second control function is enabled.

25. A method according to claim 24 wherein the communicating step includes providing a first usage key card for the first treatment device and a second usage key card for the second treatment device, each usage key card adapted to be handled separate from the respective treatment device and comprising a storage medium formatted to contain, for the respective treatment device, the identification code and the functional code that, upon reading by the reader, is downloaded to the controller.

* * * * *

UNITED STATES PATENT AND TRADEMARK OFFICE
CERTIFICATE OF CORRECTION

PATENT NO. : 6,783,523 B2  Page 1 of 1
APPLICATION NO. : 10/212311
DATED : August 31, 2004
INVENTOR(S) : Jay Qin et al.

It is certified that error appears in the above-identified patent and that said Letters Patent is hereby corrected as shown below:

On the title page item (56), col. 2, line 2, under "Other Publications" in the Castell reference after "current" delete "Stragegies" and substitute -- Strategies --.

On the title page item (56), page 2, col. 2, line 10, under "References Cited" insert -- 5,423,811, Imran, 13 June 1995 --.

In column 22, line 25, after "data" delete "stare" and substitute -- state --.

In column 24, line 44, after "pre-established" delete "wanner" and substitute -- manner --.

Signed and Sealed this

Eighth Day of January, 2008

JON W. DUDAS
*Director of the United States Patent and Trademark Office*